(12) United States Patent
Ewanicki et al.

(10) Patent No.: US 7,232,910 B2
(45) Date of Patent: Jun. 19, 2007

(54) METHODS OF PREPARING INDAZOLE COMPOUNDS

(75) Inventors: Brigitte Leigh Ewanicki, Encinitas, CA (US); Erik Jon Flahive, San Diego, CA (US); Annie Judith Kasparian, Oceanside, CA (US); Mark Bryan Mitchell, San Diego, CA (US); Michael David Perry, Santee, CA (US); Stacy Ann O'Neill-Slawecki, San Diego, CA (US); Neal William Sach, La Jolla, CA (US); James Edward Saenz, Kalamazoo, MI (US); Bing Shi, San Diego, CA (US); Nebojsa Slobodan Stankovic, San Diego, CA (US); Jayaram Kasturi Srirangam, San Diego, CA (US); Qingping Tian, San Diego, CA (US); Shu Yu, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 11/264,440

(22) Filed: Oct. 31, 2005

(65) Prior Publication Data

US 2006/0094881 A1 May 4, 2006

Related U.S. Application Data

(60) Provisional application No. 60/717,071, filed on Sep. 14, 2005, provisional application No. 60/624,635, filed on Nov. 2, 2004.

(51) Int. Cl.
*C07D 401/12* (2006.01)
(52) U.S. Cl. .................................. 546/275.7
(58) Field of Classification Search ............. 546/275.7
See application file for complete search history.

(56) References Cited

U.S. PATENT DOCUMENTS

| 6,531,491 | B1 | 3/2003 | Kania et al. |
| 6,534,524 | B1 | 3/2003 | Kania et al. |
| 2004/0192653 | A1 | 9/2004 | Munson et al. |
| 2004/0224988 | A1 | 11/2004 | Freddo et al. |

FOREIGN PATENT DOCUMENTS

WO  WO 2006/123223  11/2006

OTHER PUBLICATIONS

Vippagunta et al., "Crystalline solids", Advanced Drug Delivery Reviews, 48 (2001), 3-26.*
Guillory "Generation of polymorphs, etc.,"in Brittain. (ed.), Polymorphism in Pharmaceutical Solids, vol. 95, Marcel Dekker, NY. 1999, pp. 183-226.*

* cited by examiner

*Primary Examiner*—Patricia L. Morris
(74) *Attorney, Agent, or Firm*—Matthew J. Pugmire; Bryan C. Zielinski

(57) ABSTRACT

The present invention relates to methods for preparing indazole compounds of formula I, which are useful as modulators and/or inhibitors of protein kinases.

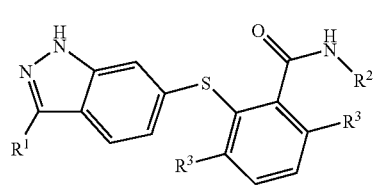

The present invention also relates to intermediate compounds useful in the preparation of compounds of formula I.

4 Claims, No Drawings

US 7,232,910 B2

METHODS OF PREPARING INDAZOLE COMPOUNDS

This application claims priority to U.S. Provisional Application No. 60/624,635, filed Nov. 2, 2004, and to U.S. Provisional Application No. 60/717,071, filed on Sep. 14, 2005, which are both incorporated herein by reference in their entirety.

FIELD OF THE INVENTION

The present invention relates to methods for preparing indazole compounds, and intermediates thereof, which are useful as modulators and/or inhibitors of protein kinases.

BACKGROUND OF THE INVENTION

The present invention relates to methods of preparing indazole compounds, and intermediate compounds thereof, that are useful as inhibitors of protein kinases. U.S. Pat. Nos. 6,534,524 and 6,531,491, which are both incorporated herein by reference in their entirety, are directed to indazole compounds that modulate and/or inhibit the activity of certain protein kinases such as VEGF-R (vascular endothelial cell growth factor receptor), FGF-R (fibroblast growth factor receptor), CDK (cyclin-dependent kinase) complexes, CHK1, LCK (also known as lymphocyte-specific tyrosine kinase), TEK (also known as Tie-2), FAK (focal adhesion kinase), and/or phosphorylase kinase. Such compounds are useful for the treatment of cancer and other diseases associated with angiogenesis or cellular proliferation mediated by protein kinases. One group of indazole compounds discussed in U.S. Pat. No. 6,534,524 can be represented by the formula shown below:

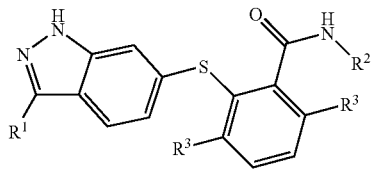

Although methods of preparing such compounds were previously referred to in U.S. Pat. Nos. 6,534,524 and 6,531,491, there remains a need in the art for new synthetic routes that are efficient and cost effective.

The discussion of the background to the invention herein is included to explain the context of the present invention. This is not to be taken as an admission that any of the material referred to was published, known, or part of the common general knowledge in any country as of the priority date of any of the claims.

SUMMARY

The present invention relates to methods of preparing compounds of formula 1

1 or pharmaceutically acceptable salts or solvates thereof, wherein: $R^1$ is CH=CH—$R^4$, or CH=N—$R^4$, and $R^1$ is substituted with 0 to 4 $R^5$ groups; $R^2$ is ($C_1$ to $C_{12}$) alkyl, ($C_3$ to $C_{12}$) cycloalkyl, (5 to 12-membered) heterocycloalkyl, ($C_6$ to $C_{12}$) aryl, (5 to 12-membered) heteroaryl, ($C_1$ to $C_{12}$) alkoxy, ($C_6$ to $C_{12}$) aryloxy, ($C_3$ to $C_{12}$) cycloalkoxy, NH—($C_1$ to $C_8$ alkyl), NH—($C_6$ to $C_{12}$ aryl), NH-(5 to 12-membered heteroaryl), N=CH—($C_1$ to $C_{12}$ alkyl), NH(C=O)$R^5$, or $NH_2$, and $R^2$ is substituted with 0 to 4 $R^5$ groups; each $R^3$ is independently hydrogen, halogen, or ($C_1$ to $C_8$) alkyl, and the ($C_1$ to $C_8$) alkyl is substituted with 0 to 4 $R^5$ groups; $R^4$ is ($C_1$ to $C_{12}$) alkyl, ($C_3$ to $C_{12}$) cycloalkyl, (5 to 12-membered) heterocycloalkyl, ($C_6$ to $C_{12}$) aryl, (5 to 12-membered) heteroaryl, and $R^4$ is substituted with 0 to 4 $R^5$ groups; and each $R^5$ is independently halogen, ($C_1$ to $C_8$) alkyl, —OH, —$NO_2$, —CN, —$CO_2$H, —O—($C_1$ to $C_8$ alkyl), ($C_6$ to $C_{12}$) aryl, aryl ($C_1$ to $C_8$) alkyl, —$CO_2CH_3$, —$CONH_2$, —$OCH_2CONH_2$, —$NH_2$, —$SO_2NH_2$, halo ($C_1$ to $C_{12}$) alkyl, or —O-halo ($C_1$ to $C_{12}$) alkyl; the method comprising reacting a compound of formula 2 with a compound of formula $R^1H$

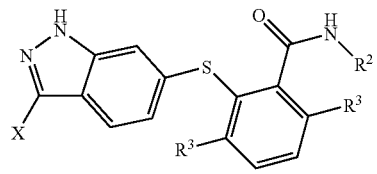

2 wherein X is an activated substituent group, to form the compound of formula 1. In one embodiment $R^1$ is CH=CH-(5 to 12-membered) heteroaryl. In a further embodiment the (5 to 12-membered) heteroaryl group in $R^1$ is pyridinyl. In another embodiment $R^2$ is ($C_1$ to $C_{12}$) alkyl. In a further embodiment $R^2$ is methyl. In another embodiment each $R^3$ is hydrogen. In one embodiment, the reaction described above is carried out under conditions comprising a catalyst. In one embodiment the catalyst is Pd or Cu. In a further embodiment the catalyst is Pd(OAc)$_2$, and the reaction conditions further comprise a ligand that complexes with the Pd catalyst. One embodiment the ligand is P(o-Tol)$_3$. In a further embodiment the reaction conditions further comprise dimethylacetamide as a solvent, Proton Sponge as a base, LiBr as an additive, and the reaction is carried out at 110° C.

Another aspect of the present invention relates to a method of preparing a compound of formula 1-a, or a pharmaceutically acceptable salt or solvate thereof, 1-a

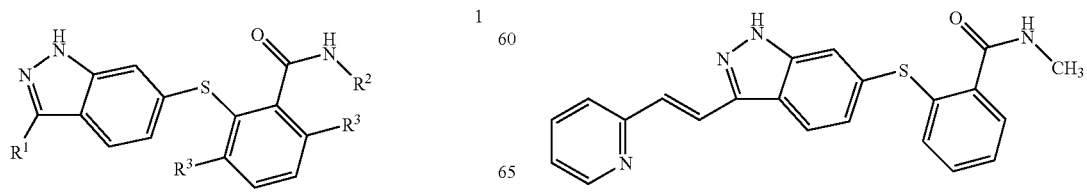

the method comprising reacting a compound of formula 2-a with a compound of formula 6

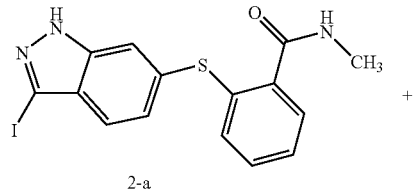

2-a

+

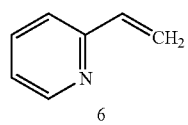

6 to form the compound of formula 1-a. In one particular embodiment, this reaction is carried out under conditions comprising Pd or Cu as a catalyst. In one embodiment the catalyst is Pd(OAc)$_2$, and wherein the reaction conditions further comprise P(o-Tol)$_3$ as a ligand that complexes with the Pd catalyst. In a further embodiment the reaction conditions further comprise Proton Sponge as a base, LiBr as an additive, and dimethylacetamide or N-methyl-2-pyrrolidone as a solvent, and wherein the reaction is carried out at a temperature of 100 to 120° C. In one embodiment the reaction is carried out at 110° C.

The present invention also relates to a compound of the formula 2

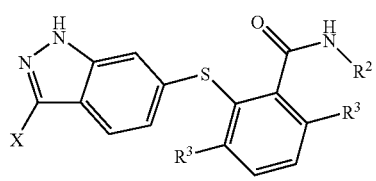

2 where $R^2$, $R^3$, and X are as defined above, or a pharmaceutically acceptable salt or solvate thereof. In one embodiment of the invention is a compound of formula 2a

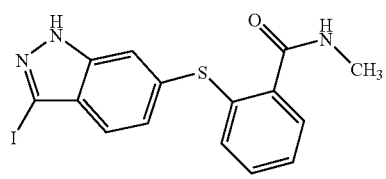

2a or a pharmaceutically acceptable salt or solvate thereof.

The present invention also relates to a method of preparing a compound of formula 2, or a pharmaceutically acceptable salt or solvate thereof, comprising reacting a compound of formula 3 with a compound of formula 4

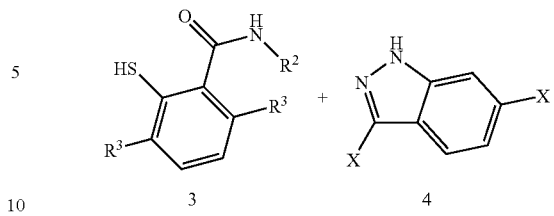

3      4 wherein $R^2$, $R^3$, and X are as defined above. In one particular embodiment $R^2$ is ($C_1$ to $C_{12}$) alkyl. In another particular embodiment $R^2$ is methyl. In another particular embodiment each $R^3$ is hydrogen. In another particular embodiment each X is iodine. In a further embodiment the reaction is carried out under conditions comprising a catalyst. In one particular embodiment the catalyst is Pd or Cu. In a further embodiment the catalyst is Pd$_2$(dba)$_3$, and the reaction conditions further comprise a ligand that complexes with the Pd catalyst. In a further embodiment the ligand is Xantphos. In a further embodiment the reaction conditions further comprise dimethylformamide as a solvent, CsOH as a base, and the reaction is carried out at 70° C.

Another aspect of the present invention relates to a method of preparing the compound of formula 2a, or a pharmaceutically acceptable salt or solvate thereof, comprising reacting the compound of formula 3-a with the compound of formula 4-a.

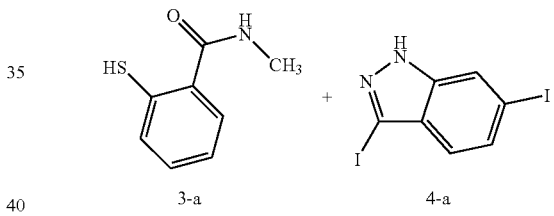

3-a      4-a

In a further embodiment the reaction is carried out under conditions comprising Pd or Cu as a catalyst. In a further embodiment the catalyst is Pd$_2$(dba)$_3$, and the reaction conditions further comprise Xantphos as a ligand that complexes with the Pd catalyst. In a further embodiment the reaction conditions further comprise CsOH as a base, and dimethylacetamide or N-methyl-2-pyrrolidone as a solvent, and the reaction is carried out at a temperature of 60 to 80° C. For example, the reaction can be carried out at 70° C.

The present invention further relates to a method of preparing a compound of formula 4-a, or a pharmaceutically acceptable salt or solvate thereof, by reacting a compound of formula 5-a with I$_2$.

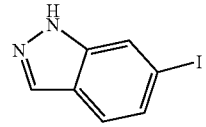

5-a

Another aspect of the present invention relates to compounds of formula 7, or a pharmaceutically acceptable salt or solvate thereof

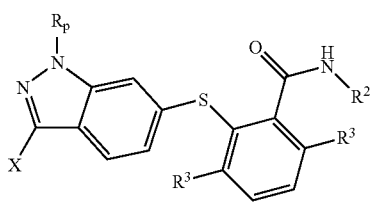

where $R^2$, $R^3$ and X are as defined as above, and where $R_p$ is a suitable protecting group. In a particular embodiment is a compound of formula 7-a

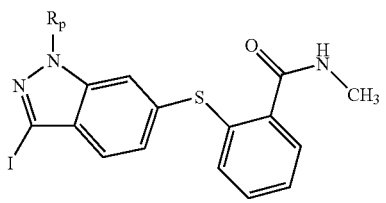

where $R_p$ is THP or Boc, or a pharmaceutically acceptable salt or solvate thereof. In a further embodiment is a compound of formula 7a where $R_p$ is THP. In a further embodiment $R_p$ is Boc.

The present invention further relates to a compound of formula 8

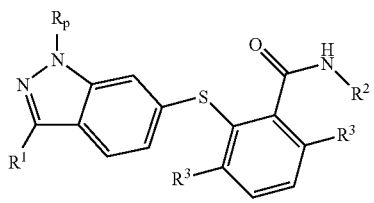

where $R^1$, $R^2$, $R^3$, and $R_p$ are as defined above, or a pharmaceutically acceptable salt or solvate thereof. In a particular embodiment the invention relates to a compound of formula 8-a

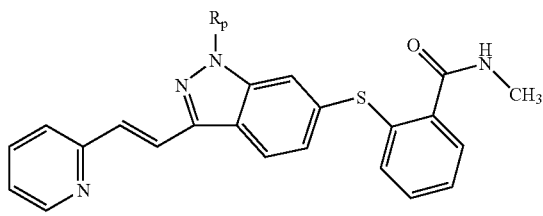

where $R_p$ is a suitable protecting group, or a pharmaceutically acceptable salt or solvate thereof. In one particular embodiment $R_p$ is tetrahydropyran. In a further particular embodiment $R_p$ is Boc.

In another aspect of the present invention is a method for preparing a compound of formula 1, or a pharmaceutically acceptable salt or solvate thereof,

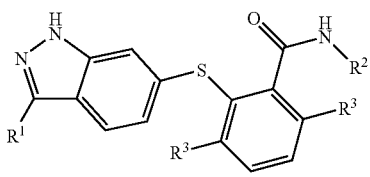

where $R^1$, $R^2$, and $R^3$ are as defined above, the method comprising deprotecting a compound of formula 8

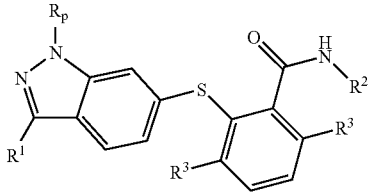

where $R_p$ is a suitable protecting group. In one particular embodiment is a method of preparing a compound of formula 1-a, or a pharmaceutically acceptable salt or solvate thereof

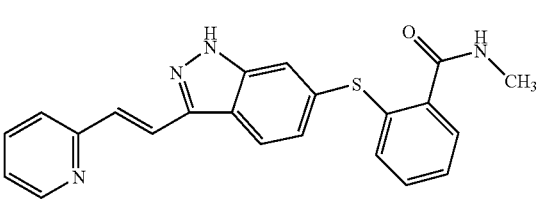

the method comprising deprotecting a compound of formula 8-a

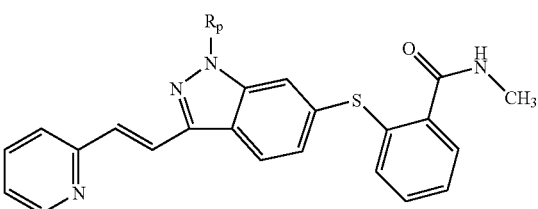

wherein $R_p$ is a suitable protecting group. In one embodiment $R_p$ is THP. In another embodiment $R_p$ is Boc. In a further embodiment the deprotecting is carried out under conditions comprising TsOH and MeOH. In a further embodiment the deprotecting is carried out under conditions comprising trifluoroacetic acid.

In another aspect of the present invention is a method of preparing a compound of formula 8, or a pharmaceutically acceptable salt or solvate thereof

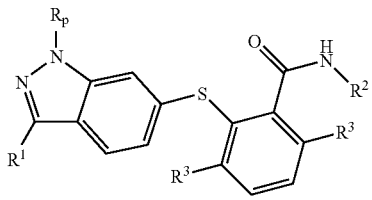

8 where $R^1$, $R^2$, $R^3$, and $R_p$ are as defined previously, the method comprising reacting a compound of formula 7 with a compound of formula $R^1H$

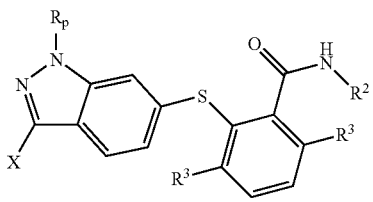

7 where X is an activated substituent group, to form the compound of formula 8. In one particular embodiment is a method for preparing a compound of formula 8-a, or a pharmaceutically acceptable salt or solvate thereof

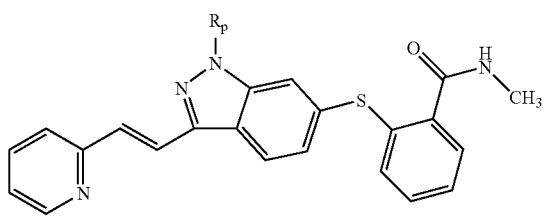

8-a wherein $R_p$ is a suitable protecting group, the method comprising reacting a compound of formula 7-a with a compound of formula 6

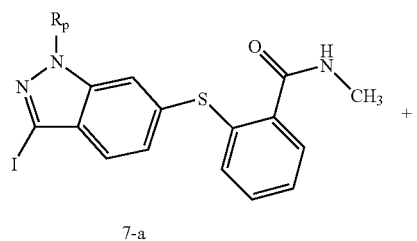

7-a

+

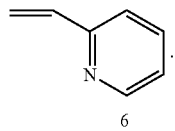

6

In one particular embodiment $R_p$ is tetrahydropyran. In a further particular embodiment $R_p$ is Boc. In a further particular embodiment the reaction is carried out under conditions comprising a catalyst. In a further particular embodiment the catalyst is Pd or Cu. In a further particular embodiment the catalyst is $Pd(OAc)_2$, and the reaction conditions further comprise a ligand that complexes with the Pd catalyst. In a further particular embodiment the ligand is $P(o\text{-}Tol)_3$. In a further particular embodiment the reaction conditions further comprise dimethylformamide as a solvent, $(i\text{-}Pr)_2NEt$ as a base, and the reaction is carried out at 100° C. In a further embodiment the catalyst is $Pd(OAc)_2$, and wherein the reaction conditions further comprise $P(o\text{-}Tol)_3$ as a ligand that complexes with the Pd catalyst, dimethylformamide or N-methyl-2-pyrrolidone as a solvent, $(i\text{-}Pr)_2NEt$ as a base, and wherein the reaction is carried out at a temperature of 90 to 110° C.

In another aspect of the present invention is a method of preparing a compound of formula 7, or a pharmaceutically acceptable salt or solvate thereof

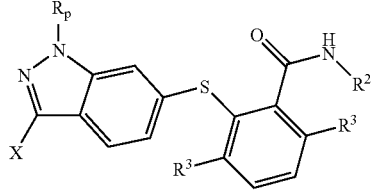

7 where $R^2$, $R^3$, $R_p$, and X are as defined above, the method comprising adding a suitable protecting group $R_p$ to a compound of formula 2.

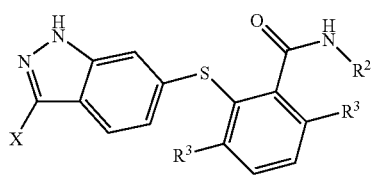

2

In one particular embodiment is a method of preparing a compound of formula 7-a, or a pharmaceutically acceptable salt or solvate thereof

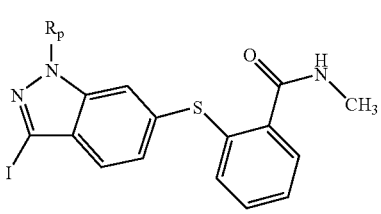

7-a where $R_p$ is a suitable protecting group, the method comprising protecting a compound of formula 2-a with a suitable protecting group.

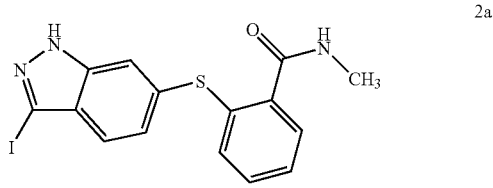

2a

In one particular embodiment $R_p$ is tetrahydropyran. In a further particular embodiment the protection step occurs under conditions that comprise dihydropyran, TsOH and EtOAc. In another particular embodiment $R_p$ is Boc. In a further particular embodiment the Boc protecting group is added under conditions that comprise DMAP and DMF.

Another aspect of the present invention relates to a compound of formula 10

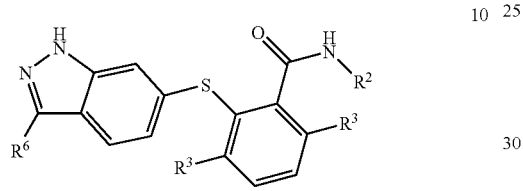

10 where $R^6$ is C≡C—$R^4$, and $R^6$ is optionally substituted with 0 to 4 $R^5$ groups, and $R^2$, $R^3$, and $R^5$ are as previously defined, or a pharmaceutically acceptable salt or solvate thereof. In one particular embodiment is compound of formula 10-a

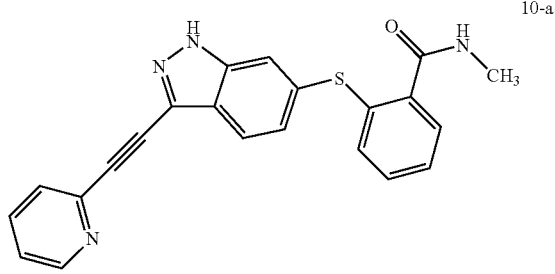

10-a or a pharmaceutically acceptable salt or solvate thereof.

Another aspect of the present invention relates to a compound of formula 11

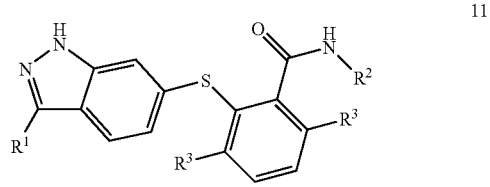

11 where $R^1$, $R^2$ and $R^3$ are as defined above and wherein the stereochemistry at the double bond in the $R^1$ substituent is designated as the Z orientation, or a pharmaceutically acceptable salt or solvate thereof. In one particular embodiment is a compound of formula 11-a

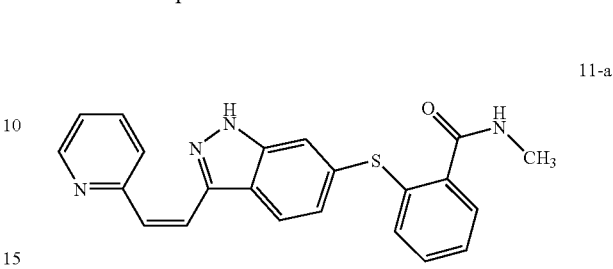

11-a or a pharmaceutically acceptable salt or solvate thereof.

Another aspect of the present invention relates to a method of preparing a compound of formula 10, or a pharmaceutically acceptable salt or solvate thereof

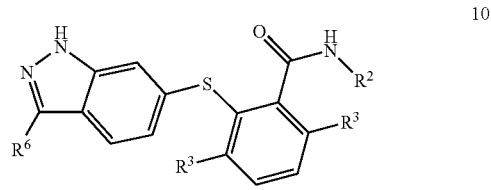

10 where $R^6$, $R^2$, and $R^3$ are as defined previously, the method comprising reacting a compound of formula 2 with a compound of formula $R^6$H

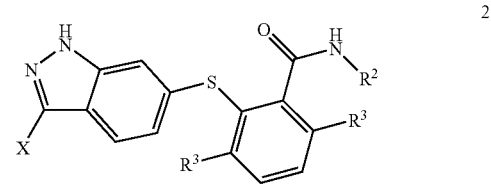

2 where X is an activated substituent group, to form the compound of formula 10. In one particular embodiment is a method of preparing a compound of formula 10-a, or a pharmaceutically acceptable salt or solvate thereof

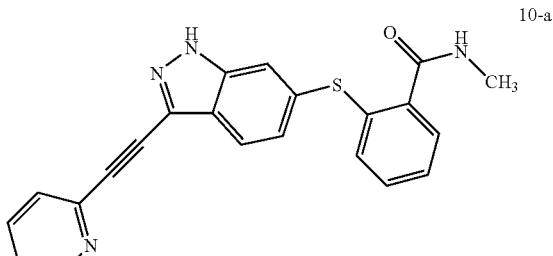

10-a the method comprising reacting a compound of formula 2-a with a compound of formula 9.

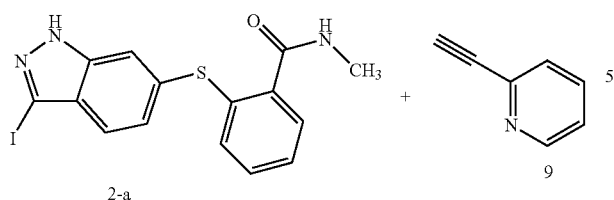

2-a

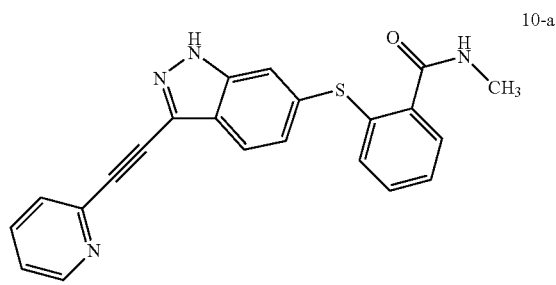

10-a

In a further particular embodiment the reaction is carried out under conditions comprising $Pd(PPh_3)_2Cl_2/CuI$ and DMF.

In another aspect of the present invention is a method of preparing a compound of formula 1, or a pharmaceutically acceptable salt or solvate thereof

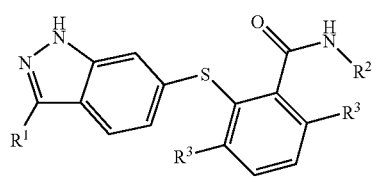

1 where $R^1$, $R^2$, and $R^3$ are as defined previously, the method comprising reacting a hydrogenating reagent with the compound of formula 10

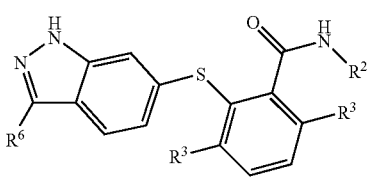

10 where $R^6$ is as defined previously. In one particular embodiment the hydrogenating reagent is $H_2NNH_2$. In a further particular embodiment the stereochemistry of the double bond in the $R^1$ substituent of formula 1 is in the E orientation. In a further particular embodiment the stereochemistry of the double bond in the $R^1$ substituent of formula 1 is in the Z orientation. In a further particular embodiment is a method of preparing a compound of formula 1-a, or a pharmaceutically acceptable salt or solvate thereof

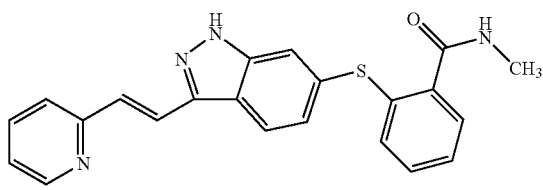

1-a the method comprising reacting a hydrogenating reagent with the compound of formula 10-a to produce the compound of formula 1-a. In one particular embodiment the hydrogenating reagent is $H_2NNH_2$.

Another aspect of the present invention is a method of preparing a compound of formula 11-a or a pharmaceutically acceptable salt or solvate thereof

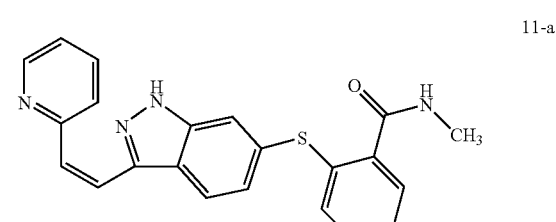

11-a the method comprising reacting a hydrogenating reagent with the compound of formula 10-a

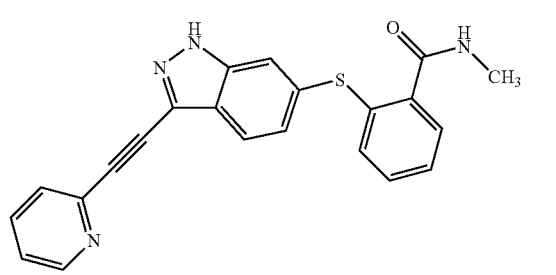

10-a to produce the compound of formula 11-a. In one particular embodiment the hydrogenating reagent is $H_2NNH_2$.

Another aspect of the present invention relates to a method of preparing a compound of formula 1, or a pharmaceutically acceptable salt or solvate thereof

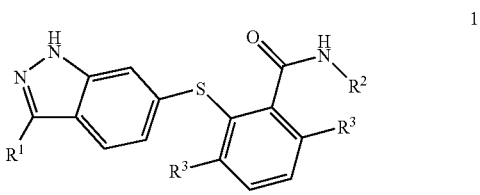

1 where $R^1$, $R^2$, and $R^3$ are as defined previously, and where the stereochemistry at the double bond in the $R^1$ substituent of formula 1 is designated E, the method comprising exposing a compound of formula 1, wherein the stereochemistry at the double bond in the $R^1$ substituent is designated Z, to ultraviolet light or to heat. In one particular embodiment is a method of preparing a compound of formula 1-a, or a pharmaceutically acceptable salt or solvate thereof

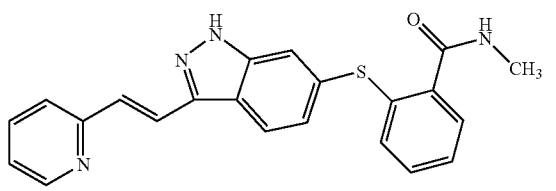

1-a the method comprising exposing a compound of formula 11-a to ultraviolet light or to heat.

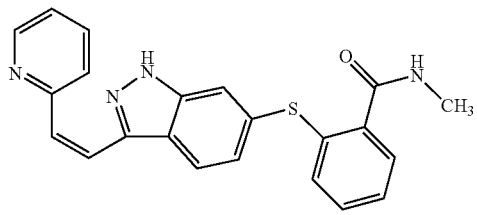

11-a

Another aspect of the present invention relates to a method of preparing a compound of formula 2-a

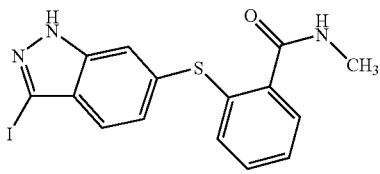

2a or a pharmaceutically acceptable salt or solvate thereof, the method comprising reacting a compound of formula 12

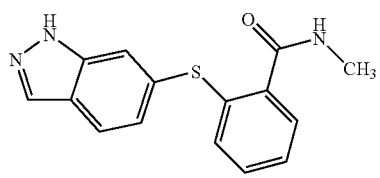

12 with $I_2$ to produce the compound of formula 2-a. In one embodiment the reaction is carried out under conditions comprising a base and a solvent. In a further embodiment the base is KOH and the solvent is N-methyl-2-pyrrolidone.

A further aspect of the present invention is a compound of formula 12

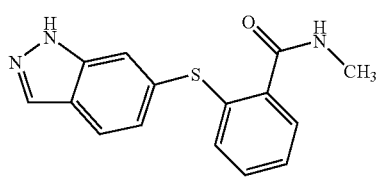

12 or a pharmaceutically acceptable salt or solvate thereof.

Another aspect of the present invention relates to a method of preparing a compound of formula 12, or a pharmaceutically acceptable salt or solvate thereof, the method comprising reacting a compound of formula 3-a with a compound of formula 5-a

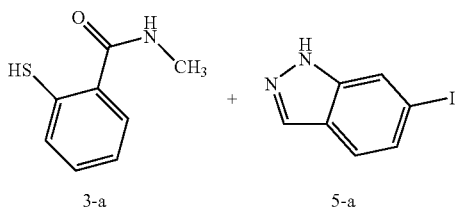

3-a    5-a to produce a compound of formula 12. In one embodiment the reaction is carried out under conditions comprising Pd or Cu as a catalyst. In a further embodiment the catalyst is $Pd_2(dba)_3$, and the reaction conditions further comprise Xantphos as a ligand that complexes with the Pd catalyst. In a further embodiment the reaction conditions further comprise CsOH as a base, and dimethylacetamide or N-methyl-2-pyrrolidone as a solvent, and the reaction is carried out at a temperature of 70 to 90° C. In one particular embodiment the reaction is carried out at a temperature of 80° C.

Another aspect of the present invention relates to a method for reducing the amount of palladium in an organic phase, the method comprising contacting the organic phase with 1,2-diaminopropane and DIPHOS to afford an organic phase wherein the amount of palladium is less than in the organic phase prior to contacting with said 1,2-diaminopropane and DIPHOS. In a particular embodiment, the amount of palladium in the organic phase after contacting with said 1,2-diaminopropane and DIPHOS is less than 1000 ppm. Even more particularly, the amount of palladium is less than 500 ppm, less than 300 ppm, less than 100 ppm, less than 50 ppm, or less than 10 ppm. In a particular embodiment, the organic phase comprises a compound of formula 1-a and palladium. In a another embodiment, after the organic phase is contacted with said 1,2-diaminopropane and DIPHOS, the method further comprises the steps of: a) contacting the solution that results from contacting the organic phase with 1,2-diaminopropane and DIPHOS with a solvent selected from the group consisting of methanol and tetrahydrofuran; and b) separating solid material from the organic phase.

Unless otherwise stated, the following terms used in the specification and claims have the meanings discussed below. The listing in this definitions section of typical substituents is exemplary and is not intended to limit the substituents defined elsewhere within this specification and claims.

As used herein, the terms "comprising" and "including" are used in their open, non-limiting sense.

The term "reacting," as used herein, refers to a chemical process or processes in which two or more reactants are allowed to come into contact with each other to effect a chemical change or transformation. For example, when reactant A and reactant B are allowed to come into contact with each other to afford a new chemical compound(s) C, A is said to have "reacted" with B to produce C.

The term "protecting," as used herein, refers to a process in which a functional group in a chemical compound is selectively masked by a non-reactive functional group in order to allow a selective reaction(s) to occur elsewhere on said chemical compound. Such non-reactive functional groups are herein termed "protecting groups." For example, the term "hydroxyl protecting group," as used herein refers to those groups that are capable of selectively masking the reactivity of a hydroxyl (—OH) group. The term "suitable protecting group," as used herein refers to those protecting groups that are useful in the preparation of the compounds of the present invention. Such groups are generally able to be selectively introduced and removed using mild reaction conditions that do not interfere with other portions of the subject compounds. Protecting groups that are suitable for use in the processes and methods of the present invention are known to those of ordinary skill in the art. The chemical properties of such protecting groups, methods for their introduction and their removal can be found, for example, in T. Greene and P. Wuts, *Protective Groups in Organic Synthesis* (3$^{rd}$ ed.), John Wiley & Sons, NY (1999). The terms "deprotecting," "deprotected," or "deprotect," as used herein, are meant to refer to the process of removing a protecting group from a compound. Methods for deprotecting, including the appropriate conditions and reagents, are known to those of ordinary skill in the art.

The term "activated substituent group," as used herein refers to a chemical functional group that generally allows a substitution reaction to take place at the atom to which it is attached. For example, in aryl iodides, the —I group is generally referred to as an activated substituent group because it allows substitution reactions to take place at the aryl carbon. Suitable activated substituent groups are well known, and can include halides (chloride, bromide, iodide), activated hydroxyl groups (e.g., triflate, mesylate, and tosylate), and diazonium salts.

The term "Proton Sponge" refers to N,N,N',N'-Tetramethyl-naphthalene-1,8-diamine, with the following structure

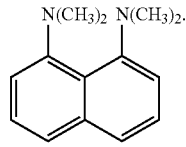

A "solvate" is intended to mean a pharmaceutically acceptable solvate form of a specified compound that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof.

As used herein, the following acronyms are defined as follows: "Et" means ethyl, "Ac" means acetyl, "Me" means methyl, "Ph" means phenyl, "Cy" means cyclohexyl, (PhO)$_2$POCl means chlorodiphenylphosphate, "HCl" means hydrochloric acid, "EtOAc" means ethyl acetate, "Na$_2$CO$_3$" means sodium carbonate, "NaOH" means sodium hydroxide, "NaCl" means sodium chloride, "NEt$_3$" means triethylamine, "THF" means tetrahydrofuran, "DIC" means diisopropylcarbodiimide, "HOBt" means hydroxy benzotriazole, "H$_2$O" means water, "NaHCO$_3$" means sodium hydrogen carbonate, "K$_2$CO$_3$" means potassium carbonate, "MeOH" means methanol, "i-PrOAc" means isopropyl acetate, "MgSO$_4$" means magnesium sulfate, "DMSO" means dimethylsulfoxide, "AcCl" means acetyl chloride, "CH$_2$Cl$_2$" means methylene chloride, "MTBE" means methyl t-butyl ether, "DMF" means N,N-dimethyl formamide, "DMA" means N,N-dimethylacetamide, "SOCl$_2$" means thionyl chloride, "H$_3$PO$_4$" means phosphoric acid, "CH$_3$SO$_3$H" means methanesulfonic acid, "Ac$_2$O" means acetic anhydride, "CH$_3$CN" means acetonitrile, "KOH" means potassium hydroxide, "P(o-Tol)$_3$" means tri-o-tolylphosphine, "THP" means tetrahydropyran, "Boc" means t-butyloxycarbonyl, "(i-Pr)$_2$NEt" means diisopropylethylamine, "Pd$_2$(dba)$_3$" means tris(dibenzylideneacetone)dipalladium(0), "TsOH" means p-toluenesulfonic acid, "Xantphos" means 9,9-Dimethyl-4,5-bis(diphenyl-phosphino)xanthene, "DIPHOS" means 1,2-bis(diphenylphosphino)ethane, "NMP" means N-methyl-2-pyrrolidone, and "DMAP" means 4-dimethylaminopyridine.

As used herein, the term "C$_1$ to C$_{12}$ alkyl" represents a straight- or branched-chain saturated hydrocarbon containing 1 to 12 carbon atoms which may be unsubstituted or substituted by one or more substituents. Examples of C$_1$ to C$_{12}$ alkyl groups include methyl, ethyl, propyl, 2-propyl, n-butyl, iso-butyl, tert-butyl, pentyl, and the like. Similarly, the term C1 to C8 alkyl refers to a straight- or branched-chain saturated hydrocarbon containing 1 to 8 carbon atoms which may be unsubstituted or substituted by one or more substituents.

The term "C$_2$ to C$_8$ alkenyl", as used herein, means an alkyl moiety comprising 2 to 8 carbons having at least one carbon-carbon double bond. The carbon-carbon double bond in such a group may be anywhere along the 2 to 8 carbon chain that will result in a stable compound. Such groups include both the E and Z isomers of said alkenyl moiety. Examples of such groups include, but are not limited to, ethenyl, propenyl, butenyl, allyl, and pentenyl. The term "allyl," as used herein, means a —CH$_2$CH=CH$_2$ group.

As used herein, the term "C$_2$-C$_8$ alkynyl" means an alkyl moiety comprising from 2 to 8 carbon atoms and having at least one carbon-carbon triple bond. The carbon-carbon triple bond in such a group may be anywhere along the 2 to 8 carbon chain that will result in a stable compound. Examples of such groups include, but are not limited to, ethyne, propyne, 1-butyne, 2-butyne, 1-pentyne, 2-pentyne, 1-hexyne, 2-hexyne, and 3-hexyne.

"C$_3$ to C$_{12}$ cycloalkyl" refers to a 3- to 12-member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group wherein one or more of the rings may contain one or more double bonds, but is non-aromatic. Examples, without limitation, of C$_3$ to C$_{12}$ cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Illustrative examples of cycloalkyl groups are derived from, but not limited to, the following:

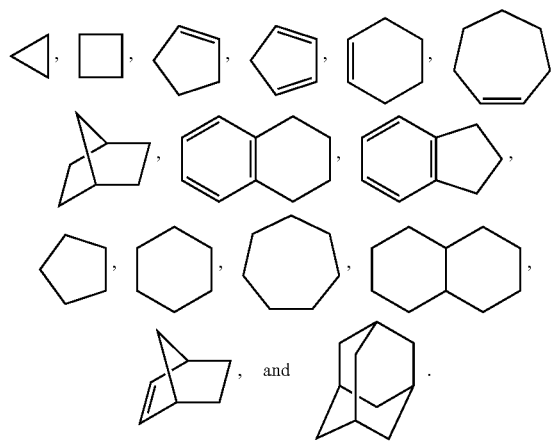

The term "$C_6$ to $C_{12}$ aryl", as used herein, means a group derived from an aromatic hydrocarbon containing from 6 to 12 carbon atoms. Examples of such groups include, but are not limited to, phenyl or naphthyl. The terms "Ph" and "phenyl," as used herein, mean a —$C_6H_5$ group. The term "benzyl," as used herein, means a —$CH_2C_6H_5$ group.

The term "5 to 12-membered heteroaryl" as used herein, means an aromatic heterocyclic group having a total of from 5 to 12 atoms in its ring, and containing from 2 to 11 carbon atoms and from 1 to 4 heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The $C_5$ to $C_{12}$ heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

Examples of typical monocyclic heteroaryl groups include, but are not limited to:

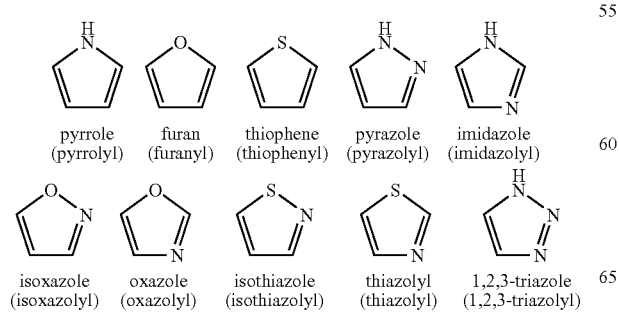

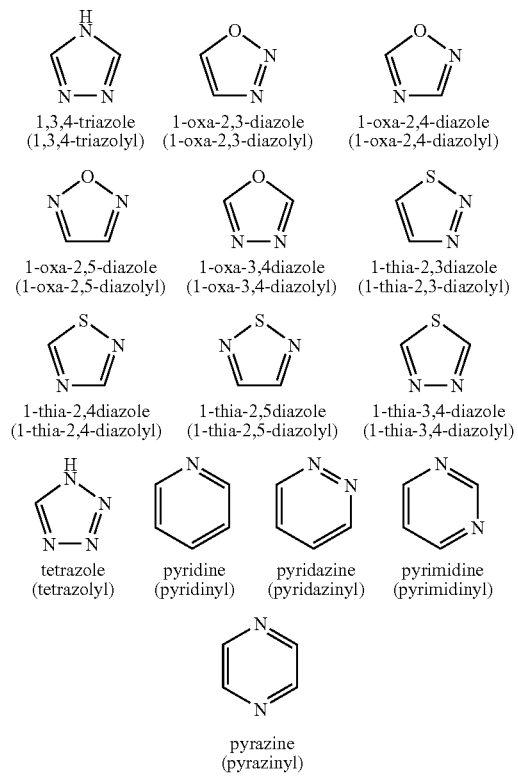

Examples of suitable fused ring heteroaryl groups include, but are not limited to:

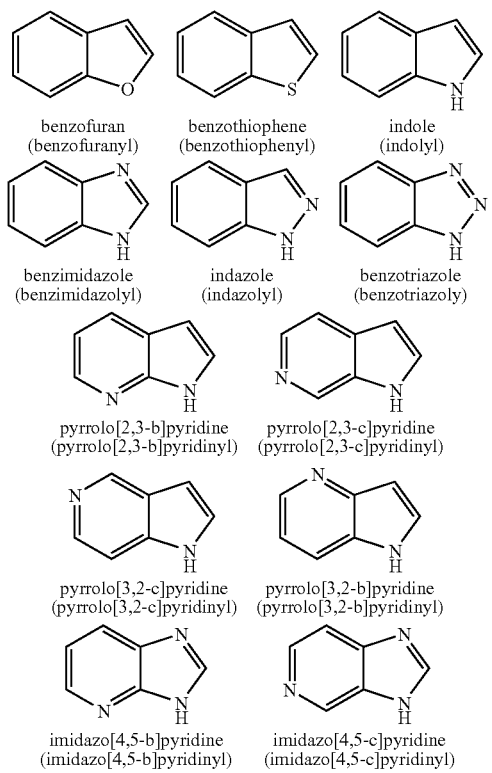

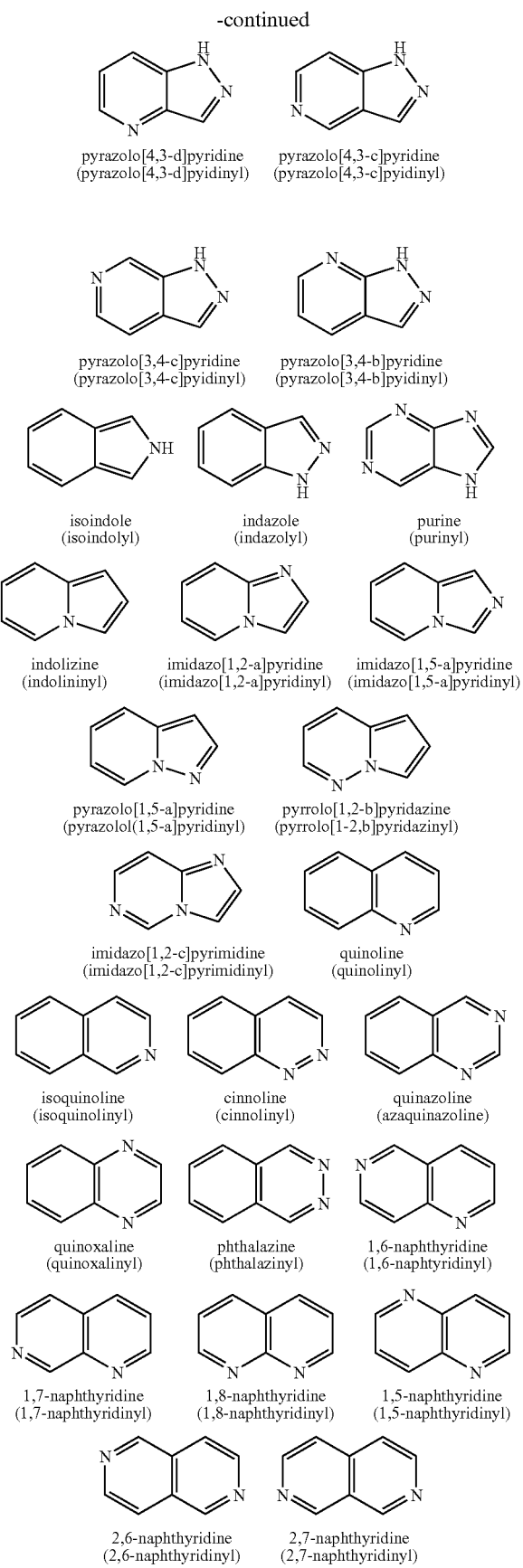

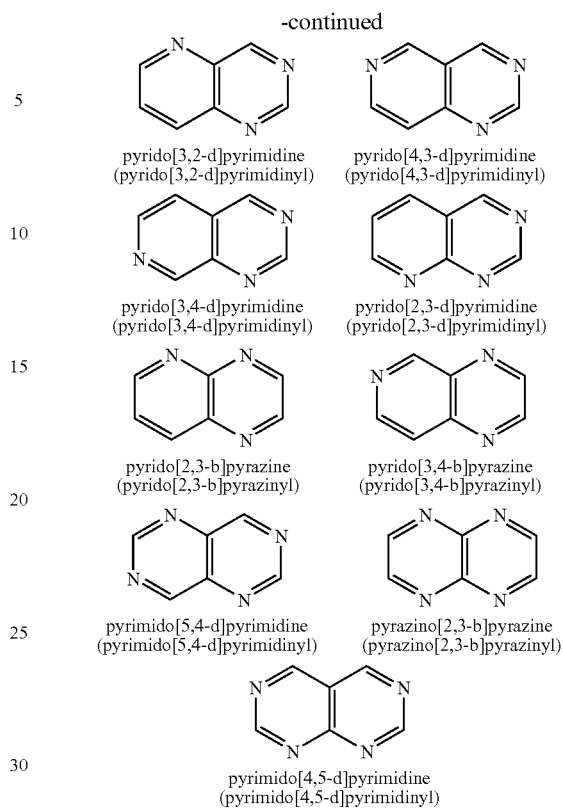

The term "5 to 12-membered heterocycloalkyl," as used herein, means a non-aromatic, monocyclic, bicyclic, tricyclic, or tetracyclic group having a total of from 5 to 12 atoms in its ring system, and containing from 2 to 11 carbon atoms and from one to four heteroatoms each independently selected from O, S and N, and with the proviso that the ring of said group does not contain two adjacent O atoms or two adjacent S atoms. Furthermore, such 5 to 12-membered heterocycloalkyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a 5 to 12-membered heterocycloalkyl group contains a sulfur atom, said sulfur atom may be oxidized with one or two oxygen atoms to afford either a sulfoxide or sulfone. An example of a 4-membered heterocyclic group is azetidinyl (derived from azetidine). An example of a 5-membered heterocyclic group is thiazolyl and an example of a 10 membered heterocyclic group is quinolinyl. Further examples of such 5 to 12-membered heterocycloalkyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

The term "$C_1$ to $C_{12}$ alkoxy" refers to an —O—($C_1$ to $C_{12}$ alkyl) group, wherein "$C_1$ to $C_{12}$ alkyl" is as defined above. Representative examples include, but are not limited to, methoxy, ethoxy, propoxy, and butoxy.

The term "$C_6$ to $C_{12}$ aryloxy" refers to an —O—($C_6$ to $C_{12}$ aryl) group, wherein "$C_6$ to $C_{12}$ aryl" is as defined herein. Representative examples include, but are not limited to, phenoxy.

The term "$C_3$ to $C_{12}$ cycloalkoxy" refers to a group —O—($C_3$ to $C_{12}$ cycloalkyl), wherein $C_3$ to $C_{12}$ cycloalkyl is as defined herein. Examples of such groups include, but are not limited to, cyclopropyloxy, cyclobutyloxy, cyclopentyloxy, and cyclohexyloxy.

The terms "halo" and/or "halogen" refer to fluorine, chlorine, bromine or iodine.

The term "3 to 12-membered heterocyclic" refers to a non-aromatic, monocyclic or fused ring group having a total of from 3 to 12 ring atoms, in which 1 to 4 ring atoms are heteroatoms selected from N, O, and $S(O)_n$ (where n is 0, 1 or 2), the remaining ring atoms being C, and with the proviso that such ring systems may not contain two adjacent O atoms or two adjacent S atoms. The rings may also have one or more double bonds. Furthermore, such groups may be bonded to the remainder of the compounds of the present invention through either a carbon atom or a heteroatom, if possible. Examples of suitable saturated heterocyclic groups include, but are not limited to:

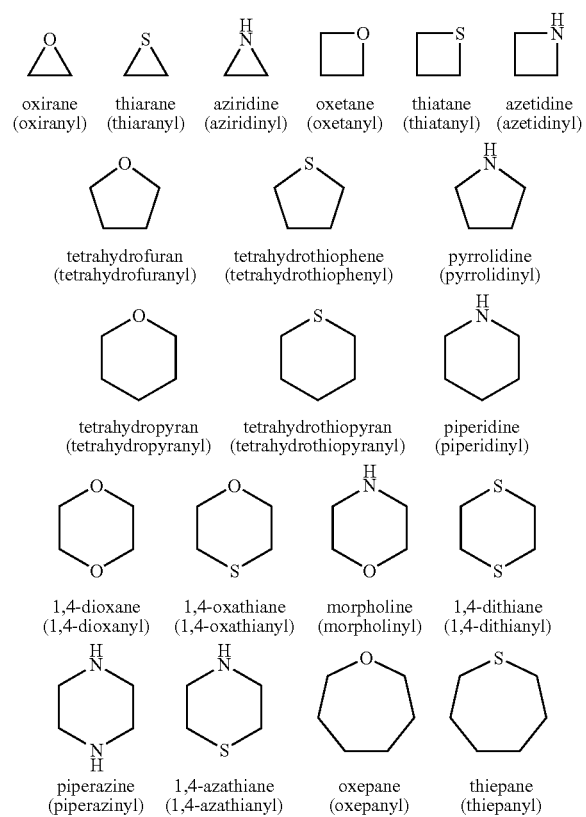

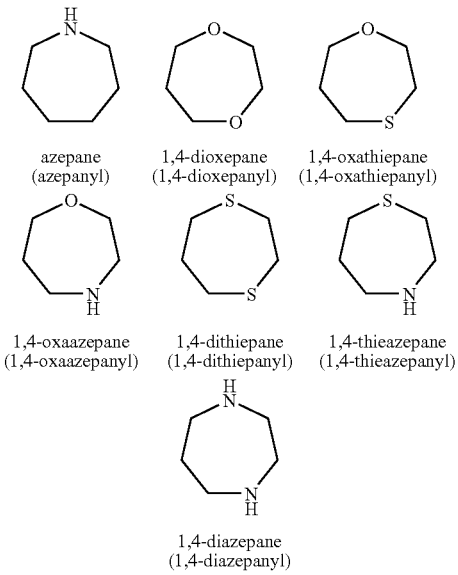

The heterocyclic group is optionally substituted with one or two substituents.

DETAILED DESCRIPTION OF THE INVENTION

The following processes illustrate the preparation of indazole compounds that are protein kinase inhibitors according to methods of the present invention. The present invention also encompasses novel intermediates that occur in the processes described herein. The compounds prepared by the methods of the present invention modulate and/or inhibit the activity of certain protein kinases. Such compounds are useful for the treatment of cancer and other diseases associated with angiogenesis or cellular proliferation mediated by protein kinases.

Unless otherwise indicated, the substituent variables of the compounds according to the following processes are as defined herein. Starting materials, the synthesis of which are not specifically described herein or provided with reference to published references, are either commercially available or can be prepared using methods known to those of ordinary skill in the art. Certain synthetic modifications may be done according to methods familiar to those of ordinary skill in the art.

Pharmaceutically acceptable salts of the present invention include acid addition and base salts (including disalts). Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodidea/odide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

In the case of agents that are solids, it is understood by those skilled in the art that the inventive compounds, agents and salts may exist in different crystal or polymorphic forms, all of which are intended to be within the scope of the present invention and specified formulas.

Compounds of the invention containing one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism. Included within the scope of the invention are all stereoisomers, geometric isomers and tautomeric forms of the inventive compounds, including compounds exhibiting more than one type of isomerism, and mixtures of one or more thereof.

One aspect of the present invention is a process for preparing indazole compounds of formula I that is depicted by the following Scheme A:

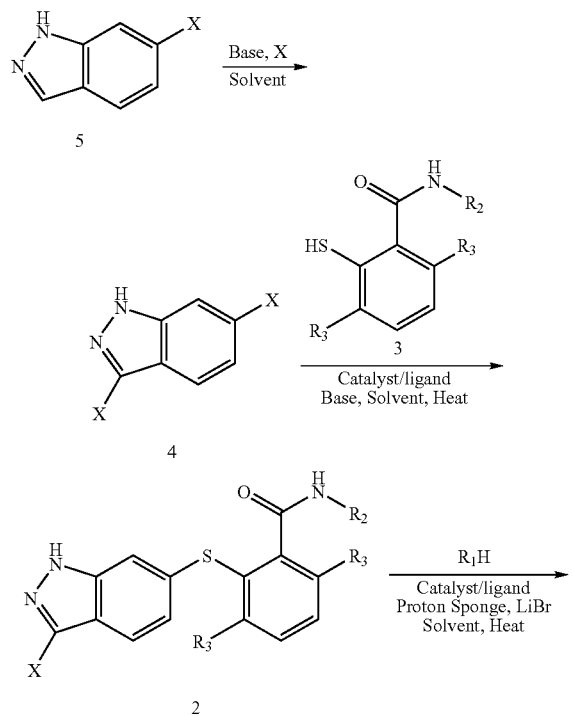

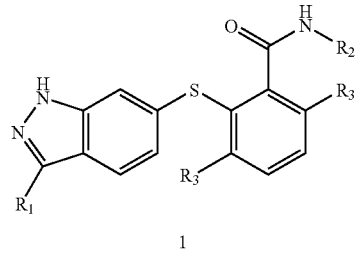

The various substituents shown above in the compounds of Scheme A are defined as follows: $R^1$ is CH=CH—$R^4$, or CH=N—$R^4$, and $R^1$ is optionally substituted with 1 to 4 $R^5$ groups; $R^2$ is $C_1$ to $C_{12}$ alkyl, $C_3$ to $C_{12}$ cycloalkyl, 5 to 12-membered heterocycloalkyl, $C_6$ to $C_{12}$ aryl, 5 to 12-membered heteroaryl, $C_1$ to $C_{12}$ alkoxy, $C_6$ to $C_{12}$ aryloxy, $C_3$ to $C_{12}$ cycloalkoxy, NH($C_1$ to $C_8$ alkyl), NH($C_6$ to $C_{12}$ aryl), NH(5 to 12-membered heteroaryl), N=CH—($C_1$ to $C_{12}$ alkyl), NH(C=O)$R^4$, or $NH_2$, and $R^2$ is optionally substituted with 1 to 4 $R^5$ groups; each $R^3$ is independently hydrogen, halogen, or $C_1$ to $C_8$ alkyl; each $R^4$ is independently $C_1$ to $C_{12}$ alkyl, $C_3$ to $C_{12}$ cycloalkyl, 5 to 12-membered heterocycloalkyl, $C_6$ to $C_{12}$ aryl, 5 to 12-membered heteroaryl, and $R^4$ is optionally substituted with 1 to 4 $R^5$ groups; each $R^5$ is independently halogen, $C_1$ to $C_{12}$ alkyl, $C_1$ to $C_{12}$ alkoxy, $C_3$ to $C_{12}$ cycloalkyl, $C_6$ to $C_{12}$ aryl, 3 to 12-membered heterocyclic, 5 to 12-membered heteroaryl, —O($C_1$ to $C_{12}$ alkyl), —O($CH_2$)$_n$($C_3$ to $C_{12}$ cycloalkyl), —O($CH_2$)$_n$($C_6$ to $C_{12}$ aryl), —O($CH_2$)$_n$(3 to 12-membered heterocyclic), —O($CH_2$)$_n$(5 to 12-membered heteroaryl) or —CN, and each hydrogen in $R^5$ is optionally substituted by one or more groups selected from halogen, —OH, —CN, $C_1$ to $C_{12}$ alkyl which may be partially or fully halogenated, —O($C_1$ to $C_{12}$ alkyl) which may be partially or fully halogenated, —CO, —SO and —$SO_2$; n is 0, 1, 2, 3 or 4; and each X is independently an activated substituent group.

In the first step of Scheme A above, compounds represented by formula 4 can be made by reacting compounds of formula 5 with an activated substituent group in the presence of a base and a suitable solvent. Bases that can be used include bases with a pKa greater than 7. Suitable solvents include polar aprotic solvents. For example, the base can be KOH, and the solvent can be DMF. Examples of activated substituent groups include halogens, such as $I_2$. This reaction can be carried out at −20° C. to 30° C. For example, this reaction can be carried out at 0° C. by immersing the reaction flask in an ice/water bath. Compounds of formula 5 can be prepared using standard reactions known in the art, such as the Sandmeyer reaction, from commercially available starting materials. For example, to prepare a compound of formula 5 where X is I6-aminoindazole (which is commercially available) can be used in a Sandmeyer reaction using potassium iodide as the iodine source.

Compounds of formula 2 can then be prepared by reacting a compound of formula 4 with a compound of formula 3. Compounds of formula 3 are commercially available. In particular embodiments of compounds of formula 3, $R^3$ can be hydrogen and $R^2$ can be $C_1$ to $C_{12}$ alkyl. For example, $R^2$ can be methyl. The coupling reaction between compounds of formula 4 and compounds of formula 3 to provide compounds of formula 2 is carried out in the presence of a catalyst, a base, and a suitable solvent. Those of skill in the art will recognize that a variety of commercially available catalysts can be used in this step, such as Cu or Pd catalysts.

Methods that use palladium or copper catalysts to couple aryl sulfides to aryl compounds containing an activated substituent X are well known. For example, palladium catalysts which are useful in the above coupling reaction include but are not limited to Pd(dppf)Cl$_2$—CH$_2$Cl$_2$, Pd[(P (t-Bu)$_3$]$_2$, Pd(PCy$_3$)$_2$Cl$_2$, Pd(P(o-tolyl)$_3$)$_2$Cl$_2$, [Pd(P(OPh-2, 4-t-Bu))$_2$Cl]$_2$, FibreCat™ 1007 (PCy$_2$-fibre/Pd(OAc)$_2$), FibreCat™ 1026 (PCy$_2$-fibre/PdCl$_2$/CH$_3$CN), FibreCat™ 1001 (PPh$_2$-fibre/Pd(OAc)$_2$), Pd(dppf)Cl$_2$, Pd(dppb)Cl$_2$, Pd(dppe)Cl$_2$, Pd(PPh$_3$)$_4$, Pd(PPh$_3$)Cl$_2$, and the like. Other useful catalysts for the above transformation include those where one or more ligands, especially phosphine ligands, additionally complexes to the palladium catalyst, for example: Pd$_2$(dba)$_3$ complexed to a phospine ligand such as 2-(tert-butyl$_2$-phosphino)biphenyl; Pd$_2$(dba)$_3$ complexed to 9,9-Dimethyl-4,5-bis(diphenyl-phosphino)xanthene (Xantphos); Pd(dba)$_2$ complexed to P(t-Bu)$_3$; Pd(OAc)$_2$ complexed to (o-biphenyl)P(t-Bu)$_2$; and Pd$_2$(dba)$_3$ complexed to (o-biphenyl)P(t-Cy)$_2$. Copper catalysts which are useful in the above coupling reaction include those catalysts in which the copper is complexed with one or more ligands, including but not limited to CuI/ethylene glycol complex; CuBr/DBU complex, Cu(PPh$_3$)Br; and Cu(PPh$_3$)Br additionally complexed to 1,10-phenanthroline or neocuproine (e.g., Cu(phen) (PPh$_3$)Br and Cu(neocup)(PPh$_3$)Br, respectively), and the like.

Bases which are useful in the above coupling reaction include but are not limited to potassium carbonate, sodium carbonate, cesium carbonate, cesium hydroxide, sodium tert-butoxide, potassium tert-butoxide, potassium phenoxide, triethylamine, and the like, or mixtures thereof. Solvents may be used in such coupling reactions including but not limited to toluene, xylenes, diglyme, tetrahydrofuran, dimethylethyleneglycol, DMF and the like, or mixtures thereof. This reaction can be carried out at a temperature of 50 to 90° C. For example, this reaction can be carried out at a temperature of 70° C.

In general, the activated substituent X in the compounds of formula 4 should be such that it provides sufficient specific reactivity to react with the compounds of formula 3 to provide the compounds of formula 2. For example, when X is I, it is observed that the iodo group at the indazole 6-position is more reactive toward oxidative addition than the iodo group at the 3-position. Compounds of formula 4 that contain such activated substituents may be prepared, isolated and/or purified, and subsequently reacted with the compounds of formula 3. Alternatively, compounds of formula 4 with suitable activated substituents may be prepared and further reacted without isolation or further purification with the compounds of formula 3 to afford the compounds of formula 2. Among suitable activated substituent groups for X are halogens (e.g., Cl, Br, and I); derivatized hydroxyl groups (e.g., triflate, mesylate, and tosylate); and diazonium salts. Other suitable activated substituent groups are known and may be found, for example, in U.S. Pat. No. 5,576,460 and in Humphrey, J. M.; Chamberlin, A. R. Chem. Rev. 97, 2243 (1997); Comprehensive Organic Synthesis; Trost, B. M., Ed.; Pergamon: New York, (1991); Vol. 6, pp 301-434; and Comprehensive Organic Transformations; Larock, R. C.; VCH: New York, (1989), Chapter 9.

The compounds produced by this coupling step, which are represented by formula 2, are novel intermediates in the synthesis of compounds of formula 1. The present invention encompasses such intermediates, as well as the corresponding pharmaceutically acceptable salts and solvates thereof. In one particular embodiment, this coupling step can be carried out as follows:

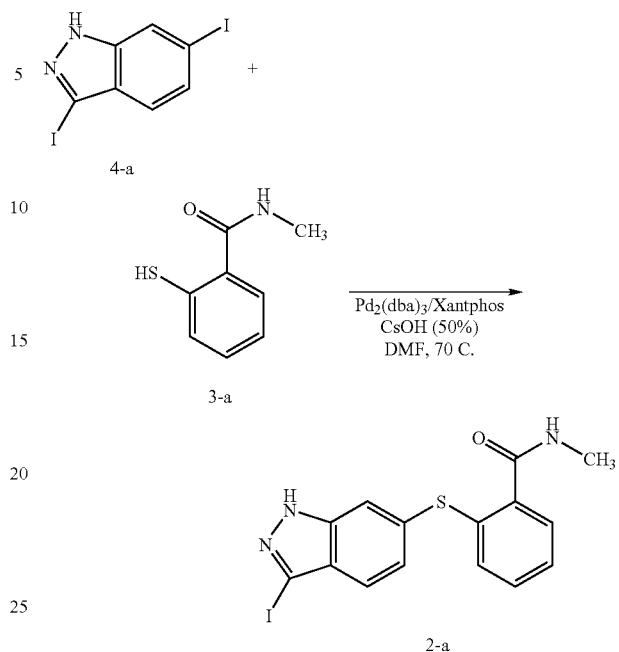

The final step in Scheme A involves a Heck reaction and is carried out by reacting a halogenide compound of formula 2 with an alkene of formula R$^1$H to produce a compound of formula 1. As indicated above, the alkene R$^1$ is CH=CH—R$^4$ or CH=N—R$^4$. For example, R$^1$ can be CH=CH—(5 to 12-membered heteroaryl). Even further, for example, the 5 to 12-membered heteroaryl of R$^1$ can be pyridinyl. In one particular embodiment, R$^1$ is 2-vinylpyridine.

A Heck reaction involves the catalytic coupling of C—C bonds, where a vinylic hydrogen is replaced by a vinyl, aryl, or benzyl group, with the latter being introduced as a halide, diazonium salt, aryl triflate or hypervalent iodo compound.

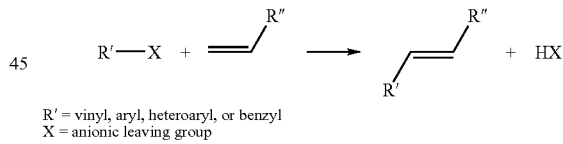

R′ = vinyl, aryl, heteroaryl, or benzyl
X = anionic leaving group

Palladium in the form of Pd(II) salts or complexes and Pd(0), with 1-5% mole concentration, is the most widely used metal catalyst for these types of reactions. A base of appropriate strength such as an inorganic base or an organic base (e.g., organic amine) is also required to neutralize the liberated acid. Beneficial additives, such as LiBr, may also be used. Typical catalysts for use in the Heck reaction include but are not limited to Pd(dppf)Cl$_2$/CH$_2$Cl$_2$, [Pd (OAc)$_2$]$_3$, trans-PdCl$_2$(CH$_3$CN)$_2$, Pd(C$_{17}$H$_{14}$O)$_x$, and Pd(0)-phosphine complexes such as Pd(PPh$_3$)$_4$ and trans-PdCl$_2$(PPh$_3$)$_2$ or in situ catalysts such as Pd(OAc)$_2$/PPh$_3$, and the like. Chelated phosphines with larger bite angles such as Cp$_2$Fe(PPh$_2$)$_2$ and Ph$_2$P(CH$_2$)$_{2-4}$PPh$_2$ are useful with catalysts such as Pd(OAc)$_2$, (pi-allyl)Pd complexes, Pd$_2$(dba)$_3$, Pd(dba)$_2$ and PdCl$_2$, and the like. The presence of phosphines "stabilize" these catalysts. Generally, these types of reactions are conducted in polar aprotic mediums (sigma donor type solvents such as acetonitrile, N,N-dimethyl formamide, dimethyl sulfoxide or dimethylacetamide). The reaction time and temperature depend on the nature of the organic halide to be activated. Iodo derivatives are more reactive and hence auxiliary ligands (phosphines) may not be required. In these cases polar solvents such as N,N-dimethyl formamide, dimethylacetamide and N-methylpyrrolidine in combination with sodium acetate as a base are especially beneficial.

Thus, as shown in Scheme A above, compounds of formula 1 can be prepared by a Heck reaction involving a compound of formula $R_1H$ that contains a vinylic hydrogen and a compound of formula 2 that contains a vinyl, aryl, heteroaryl, or benzyl group which is substituted with a halide, diazonium salt, aryl triflate or hypervalent iodo compound.

In one particular embodiment, a Heck reaction between 2-(3-Iodo-1H-indazol-6-ylsulfanyl)-N-methyl-benzamide (2-a and 2-vinyl pyridine is accomplished by heating these reactants in the presence of a catalyst such as palladium(II) acetate ($Pd(OAc)_2$), a ligand such as tri-o-tolylphosphine, a suitable base such as Proton Sponge (N,N,N',N'-Tetramethyl-naphthalene-1,8-diamine), a suitable additive such as LiBr, and a solvent such as DMA or NMP to provide N-Methyl-2-[3-(2-pyridin-2yl-vinyl)-1H-indazol-6ylsulfanyl]-benzamide (1-a), as follows.

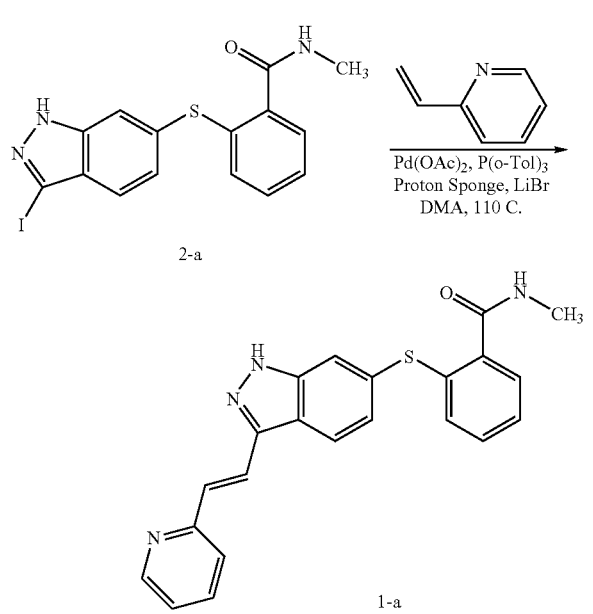

2-a 1-a

When a palladium catalyst is used in any of the above reaction steps, removal of residual palladium is an important objective. Such palladium removal can be accomplished using 10% cysteine-silica as discussed in a U.S. provisional patent application No. 60/624,719, entitled Methods for the Removal of Heavy Metals, filed on Nov. 2, 2004, and which is incorporated herein by reference in its entirety. This final step of palladium removal can also be combined with conditions that allow crystallization of the synthesized compounds in various polymorphic forms. For example, when a compound of formula 1 is prepared where $R_1$ is 2-vinylpyridine, $R_2$ is methyl, and $R_3$ are each hydrogen, the polymorphic form designated as Form IV can be produced by refluxing with THF, DMF, and MeOH, followed by the addition of HOAC and xylenes. The formation and characterization of Form IV, as well as other polymorphs, is discussed in more detail in a U.S. provisional patent application No. 60/624,665, entitled Polymorphic Forms of 6-[2-(methylcarboamoyl)phenylsulfanyl]-3-E-[2-(pyrdine-2-yl) ethenyl]indazole, filed on Nov. 2, 2004 and is incorporated herein by reference in its entirety. This palladium removal process and polymorph control step is also described in greater detail in Example 11 below.

Palladium removal can also be achieved by using 1,2-diaminopropane, or DIPHOS, which can be used alone, or in combination, as palladium scavengers to reduce the amount of palladium in an organic phase. After the addition of a palladium scavenger such as 1,2-diaminopropane and/or DIPHOS, palladium levels can be reduced further by washing with a suitable solvent such as methanol or tetrahydrofuran, followed by filtration. Such use of 1,2-diaminopropane and DIPHOS to reduce the amount of palladium is described in greater detail in Example 14 below.

In another aspect of the present invention is a process for preparing compounds of formula 1 that is depicted by the following Scheme B:

Scheme B

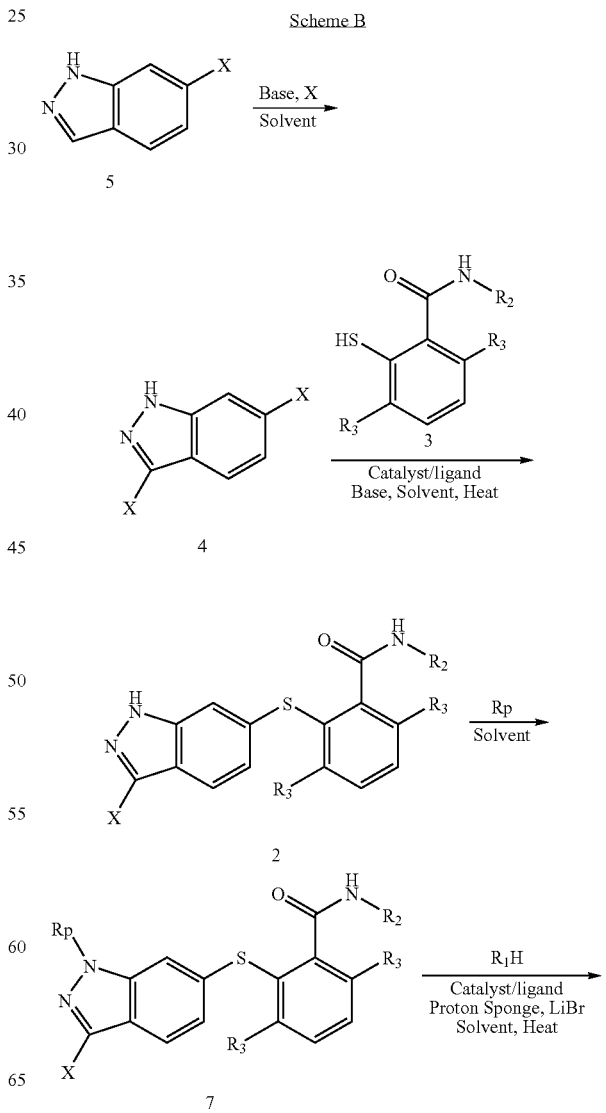

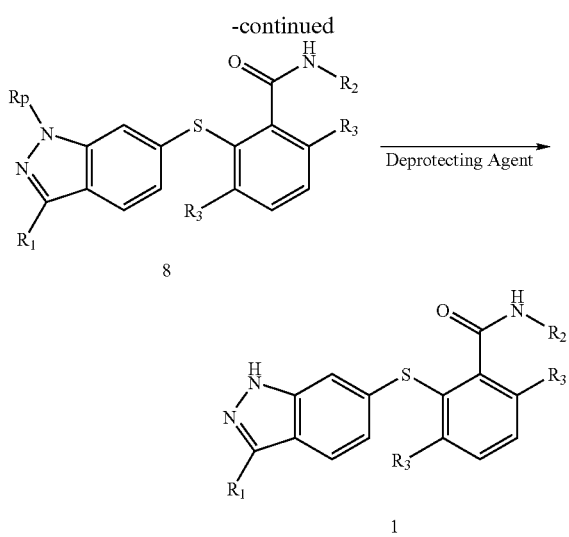

The process steps depicted above in Scheme B are similar to those described previously in Scheme A, but with a protecting step that occurs prior to the addition of the $R^1$ substituent to a compound of formula 2, and where the protecting group is subsequently removed to yield the compounds of formula 1. In the compounds shown above in Scheme B. the substituents are as defined previously in Scheme A. According to Scheme B. intermediate compounds of formula 7 are prepared by adding a suitable protecting group ($R_p$) at the N-1 position of the indazole ring in compounds of formula 2. The $R_p$ protecting group can then be removed after the addition of the $R_1$ substituent using a Heck reaction as discussed previously in Scheme A.

A suitable nitrogen protecting group, $R_p$, is one that is stable to the reaction conditions in which compounds of formula 7 are allowed to react with the compounds of formula $R_1H$ to provide the compounds of formula 8. Furthermore, such a protecting group should be chosen so that it can be subsequently removed to provide the compounds of formula 1.

Suitable nitrogen protecting groups are well known, and any nitrogen protecting group that is useful, or may be useful, in the methods of preparing the compounds of the present invention may be used. Exemplary nitrogen protecting groups include silyl, substituted silyl, alkyl ether, substituted alkyl ether, cycloalkyl ether, substituted cycloalkyl ether, alkyl, substituted alkyl, carbamate, urea, amide, imide, enamine, sulfenyl, sulfonyl, nitro, nitroso, oxide, phosphinyl, phosphoryl, silyl, organometallic, borinic acid and boronic acid groups. Examples of each of these groups, methods for protecting nitrogen moieties using these groups and methods for removing these groups from nitrogen moieties are disclosed in T. Greene and P. Wuts, supra.

Thus, suitable nitrogen protecting groups useful as $R_p$ include, but are not limited to, silyl protecting groups (e.g., SEM: trimethylsilylethoxymethyl, TBDMS: tert-butyldimethylsilyl); alkyl ether protecting groups such as cycloalkyl ethers (e.g., THP: tetrahydropyran); carbamate protecting groups such as alkyloxycarbonyl (e.g., Boc: t-butyloxycarbonyl), aryloxycarbonyl (e.g., Cbz: benzyloxycarbonyl, and FMOC: fluorene-9-methyloxycarbonyl), alkyloxycarbonyl (e.g., methyloxycarbonyl), alkylcarbonyl or arylcarbonyl, substituted alkyl, especially arylalkyl (e.g., trityl (triphenylmethyl), benzyl and substituted benzyl), and the like.

If Rp is a silyl protecting group (e.g., SEM: trimethylsilylethoxymethyl, TBDMS: tert-butyldimethylsilyl), such groups may be applied and subsequently removed under known conditions. For example, such silyl protecting groups may be attached to nitrogen moieties and hydroxyl groups via their silyl chlorides (e.g., SEMCl: trimethylsilylethoxymethyl chloride, TBDMSCl: tert-butyldimethylsilyl chloride) in the presence of a suitable base (e.g., potassium carbonate), catalyst (e.g., 4-dimethylaminopyridine (DMAP)), and solvent (e.g, N,N-dimethyl formamide). Such silyl protecting groups may be cleaved by exposure of the subject compound to a source of fluoride ions, such as the use of an organic fluoride salt such as a tetraalkylammonium fluoride salt, or an inorganic fluoride salt. Suitable fluoride ion sources include, but are not limited to, tetramethylammonium fluoride, tetraethylammonium fluoride, tetrapropylammonium fluoride, tetrabutylammonium fluoride, sodium fluoride, and potassium fluoride. Alternatively, such silane protecting groups may be cleaved under acidic conditions using organic or mineral acids, with or without the use of a buffering agent. For example, suitable acids include, but are not limited to, hydrofluoric acid, hydrochloric acid, sulfuric acid, nitric acid, acetic acid, citric acid, and methanesulfonic acid. Such silane protecting groups may also be cleaved using appropriate Lewis acids. For example, suitable Lewis acids include, but are not limited to, dimethylbromo borane, triphenylmethyl tetrafluoroborate, and certain Pd (II) salts. Such silane protecting groups can also be cleaved under basic conditions that employ appropriate organic or inorganic basic compounds. For example, such basic compounds include, but are not limited to, sodium carbonate, potassium carbonate, sodium bicarbonate, potassium bicarbonate, sodium hydroxide, and potassium hydroxide.

The cleavage of a silane protecting group may be conducted in an appropriate solvent that is compatible with the specific reaction conditions chosen and will not interfere with the desired transformation. Among such suitable solvents are, for example, alkyl esters, alkylaryl esters, aryl esters, alkyl ethers, aryl ethers, alkylaryl esters, cyclic ethers, hydrocarbons, alcohols, halogenated solvents, alkyl nitrites, aryl nitrites, alkyl ketones, aryl ketones, alkylaryl ketones, or non-protic heterocyclic compounds. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Finally, such reactions may be performed at an appropriate temperature from −20° C. to 100° C., depending on the specific reactants used. Further suitable reaction conditions may be found in T. Greene and P. Wuts, supra.

If $R_p$ is a cyclic ether protecting group (e.g., a tetrahydropyran (THP) group), such groups may be applied and subsequently removed under known conditions. For example, such cyclic ethers may be attached to nitrogen moieties and hydroxyl groups via their enol ethers (e.g., dihydropyran (DHP)) in the presence of a suitable acid (e.g., para-toluenesulfonic acid or methanesulfonic acid), and solvent (e.g., dichloromethane). Such cyclic ether groups may be cleaved by treating the subject compound with organic or inorganic acids or Lewis acids. The choice of a particular reagent will depend upon the type of ether present as well as the other reaction conditions. Examples of suitable reagents include, but are not limited to, hydrochloric acid, sulfuric acid, nitric acid, para-toluenesulfonic acid, methanesulfonic acid, or Lewis acids such as boron trifluoride etherate. If $R_p$ is a carbamate protecting group such as alkyloxycarbonyl (e.g., Boc: t-butyloxycarbonyl), or aryloxycarbonyl (e.g., Cbz: benzyloxycarbonyl) cleavage of the protecting group can be achieved under acidic conditions in the absence of water where carbamic acids are produced, which subsequently loses $CO_2$ to regenerate the amino group. Suitable acids for deprotecting such carbamate groups include, but are not limited to, trifluoroacetic acid, hydrogen chloride, TsOH, and MsOH.

These reactions may be conducted in solvents that are compatible with the specific reaction conditions chosen and will not interfere with the desired transformation. Among such suitable solvents are, for example, alkyl esters, alkylaryl esters, aryl esters, alkyl ethers, aryl ethers, alkylaryl esters, cyclic ethers, hydrocarbons, alcohols, halogenated solvents, alkyl nitriles, aryl nitriles, alkyl ketones, aryl ketones, alkylaryl ketones, or non-protic heterocyclic compounds. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent in this transformation if necessary. Finally, such reactions may be performed at an appropriate temperature from −20° C. to 100° C., depending on the specific reactants used. Further suitable reaction conditions may be found in T. Greene and P. Wuts, supra.

In one particular embodiment, a compound of formula 2-a is protected at the N-1 position of the indazole ring with tetrahydropyran (THP) to provide the nitrogen protected compound of formula 7-a as follows:

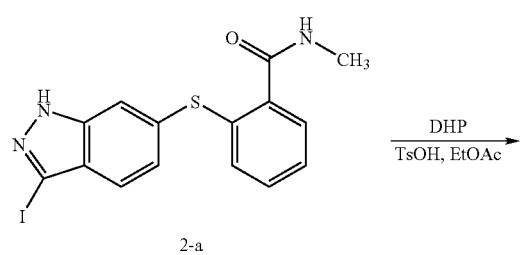

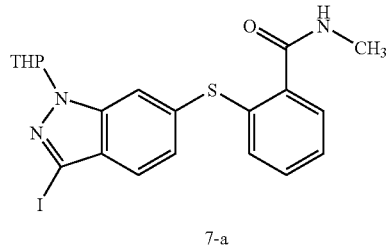

7-a

In a further particular embodiment, a compound of formula $R_1H$ can then be added to a compound of formula 7-a via the Heck reaction as discussed previously in Scheme A. For example, when $R_1H$ is 2-vinyl pyridine, the Heck reaction using the N-1 protected indaozle of formula 7-a can proceed as follows:

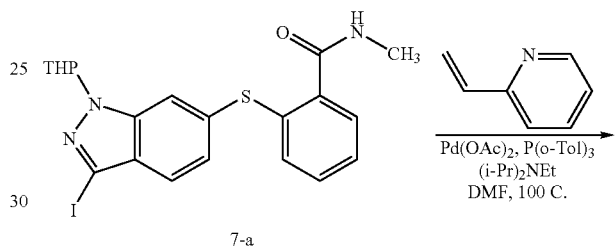

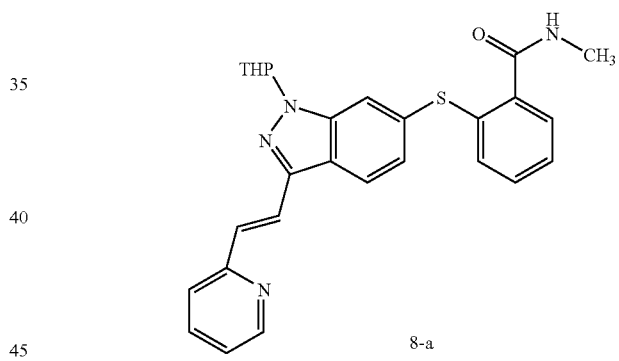

In a further particular embodiment, the resulting compound of formula 8-a can be deprotected at the N-1 position using the following conditions to provide a compound of formula 1-a:

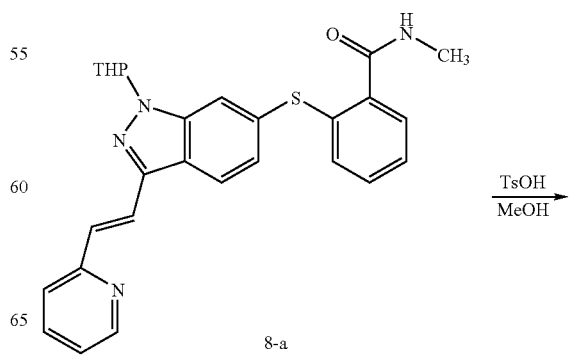

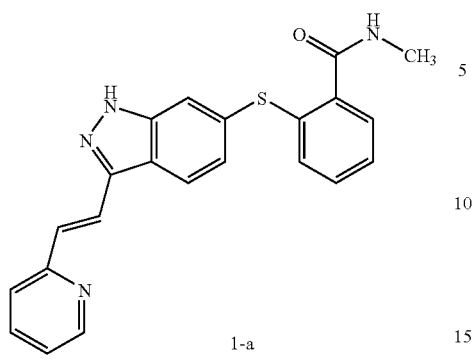

1-a

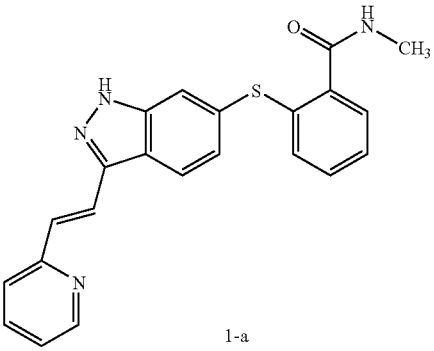

1-a

In one particular embodiment, a compound of formula 2-a is protected at the N-1 position of the indazole ring with a Boc group to provide the nitrogen protected compound of formula 7-b as follows:

In another aspect of the present invention is a process for preparing compounds of formula 1 that is depicted by the following Scheme C:

Scheme C

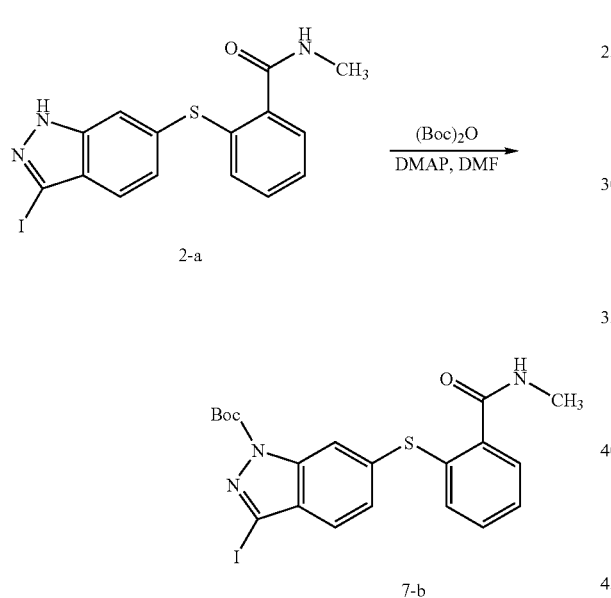

In a further particular embodiment, compounds of formula R₁H can be added to a compound of formula 7-b via the Heck reaction as discussed previously in Scheme A, and then deprotected. For example, when R₁H is 2-vinyl pyridine, the Heck reaction using the N-1 protected indaozle of formula 7-b, followed by subsequent deprotection with tri-fluoro acetic acid, can proceed as follows:

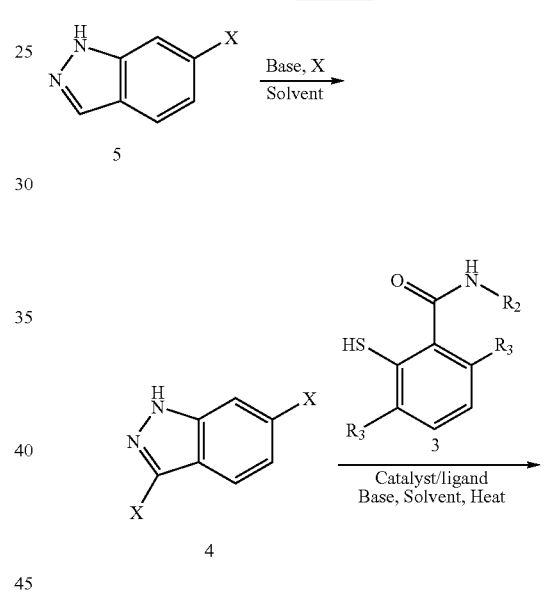

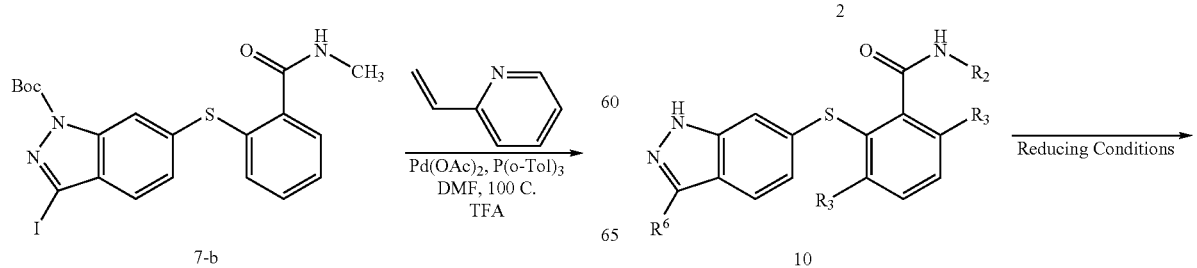

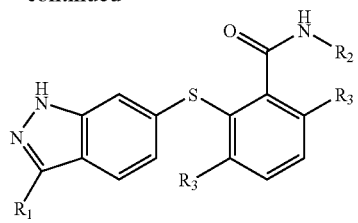

1

In the scheme shown above as Scheme C, the substituents are as previously defined as in Scheme A, and $R^6$ is C≡C—$R^4$, where $R^6$ is optionally substituted with 1 to 4 $R^5$ groups groups. The first two steps in Scheme C to provide compounds of formula 2 are similar to those shown previously in Scheme A. Compounds of formula $R^6H$ are then reacted with compounds of formula 2 to provide compounds of formula 10, where the triple bond in $R^6$ is then reduced to a double bond to provide the compounds of formula 1. The resulting double bond in the compounds of formula 1 can be either in the Z or E orientation.

The addition of $R^6H$ to compounds of formula 2 is accomplished via Sonogashira coupling, which is well known to those of skill in the art (see Sonogashira et al. *Tetrahedron Lett,* 4467 (1975); Rossi et al. *Org. Prep. Proceed. Int,* 27, 129-160 (1995)). This coupling can be carried out in the presence of a suitable catalyst, such as $Pd(PPh_3)_2Cl_2$, an additive such as CuI, and a suitable solvent such as DMF, THF, dioxane, dimethoxyethane, or toluene.

In one particular embodiment, 2-ethynylpyridine is added to a compound of formula 2-a to provide a compound of formula 10-a as follows:

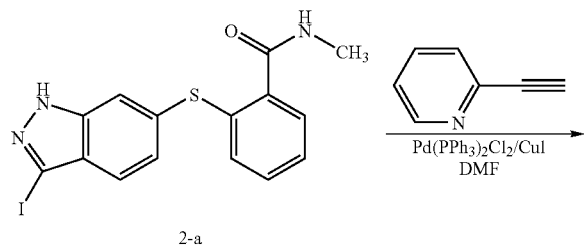

Compounds of formula 10, which contain a triple bond in the $R^6$ substituent, can then be reduced using standard hydrogenation reducing conditions known to those skilled in the art. For example, reduction of triple bonds to double bonds can be accomplished through a hydrogenation reaction using a Pd catalyst, such as Lindlar's catalyst, to afford the Z-olefine, or by using $Li/NH_3$ to give the E-olefine. The converstion between a Z-olefine to an E-olefine, and vice versa, can be carried out using procedures known to those skilled in the art (see, e.g. Okamura et al. *J. Am. Chem. Soc.* 107, 1034-1041 (1985).

In one particular embodiment, the triple bond in a compound of formula 10-a can be reduced to the Z-olefine to arrive at a compound of formula 11-a as follows:

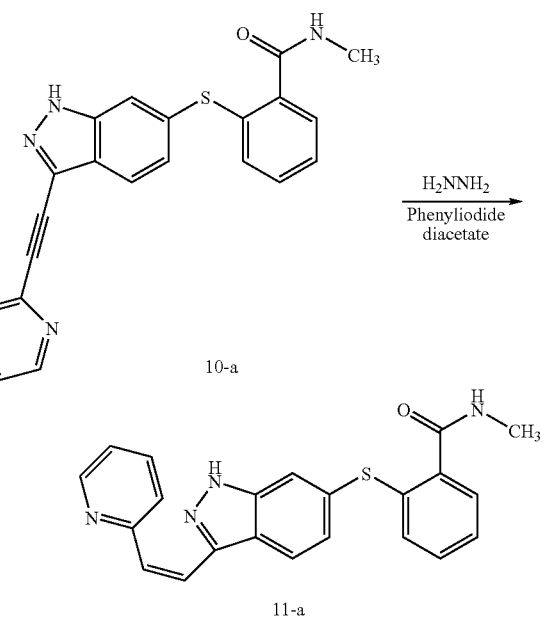

In a further embodiment, the triple bond in a compound of formula 10-a can be reduced to the E-olefine to arrive at a compound of formula 1-a as follows.

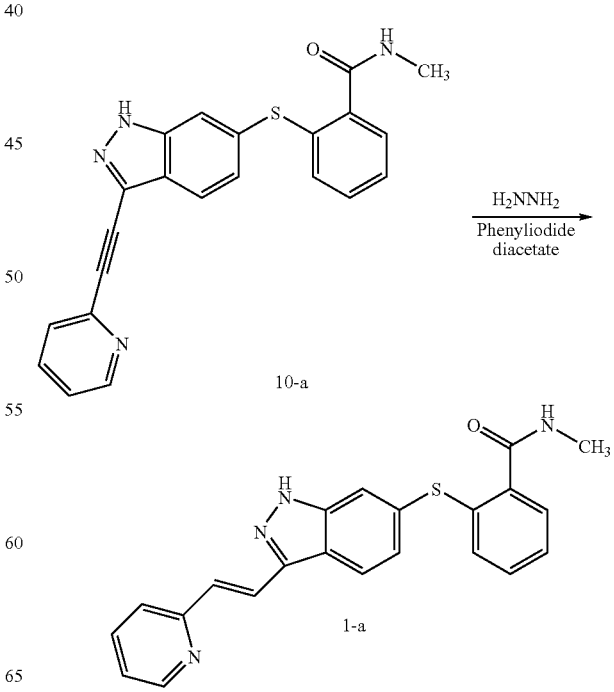

Compounds of formula 1 that are the Z-olefine can be converted to the E-olefine as discussed above. For example, in one particular embodiment, a compound of formula 11-a can be converted to a compound of formula 1-a as follows. Such isomer conversion reactions are well known to those of skill in the art.

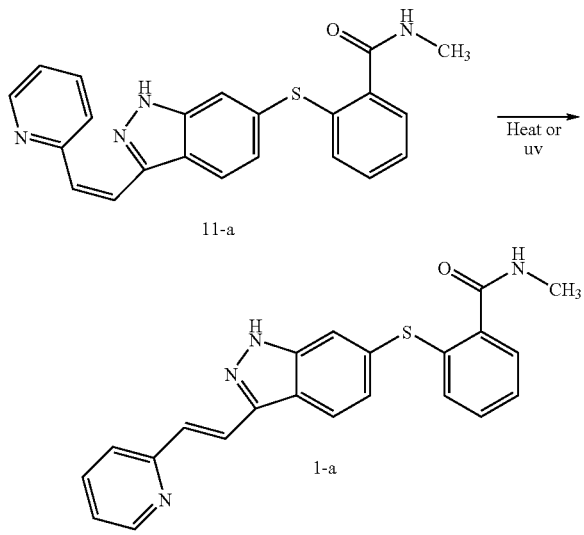

In another aspect of the present invention, a compound of formula 2-a can be prepared using the following Scheme D:

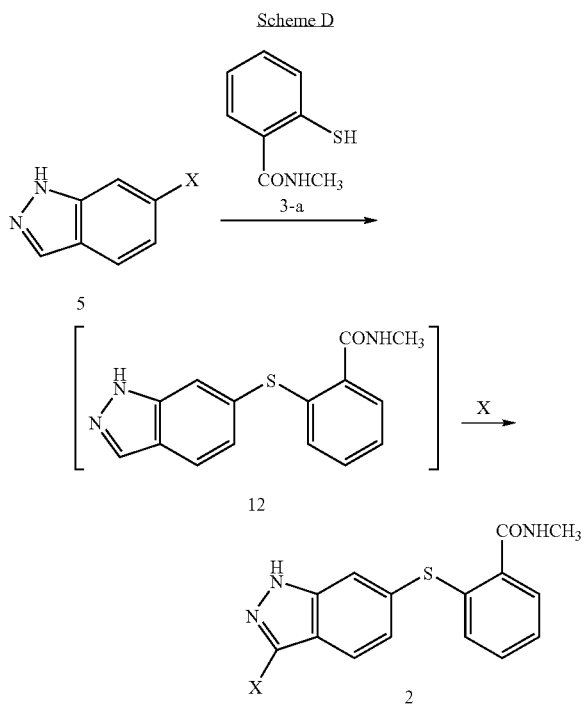

The coupling reaction between a compound of formula 5 and a compound of formula 3-a to provide a compound of formula 12 can be carried out in the presence of a catalyst, a base, and a suitable solvent. Those of skill in the art will recognize that a variety of commercially available catalysts can be used in this step, such as Cu or Pd catalysts. Methods that use palladium or copper catalysts to couple aryl sulfides to aryl compounds containing an activated substituent X are well known. For example, palladium catalysts which are useful in the above coupling reaction include but are not limited to Pd(dppf)Cl$_2$—CH$_2$Cl$_2$, Pd[(P(t-Bu)$_3$]$_2$, Pd(PCy$_3$)$_2$Cl$_2$, Pd(P(o-tolyl)$_3$)$_2$Cl$_2$, [Pd(P(OPh-2,4-t-Bu))$_2$Cl]$_2$, FibreCat™ 1007 (PCy$_2$-fibre/Pd(OAc)$_2$), FibreCat™ 1026 (PCy$_2$-fibre/PdCl$_2$/CH$_3$CN), FibreCat™ 1001 (PPh$_2$-fibre/Pd(OAc)$_2$), Pd(dppf)Cl$_2$, Pd(dppb)Cl$_2$, Pd(dppe)Cl$_2$, Pd(PPh$_3$)$_4$, Pd(PPh$_3$)Cl$_2$, and the like. Other useful catalysts for the above transformation include those where one or more ligands, especially phosphine ligands, additionally complexes to the palladium catalyst, for example: Pd$_2$(dba)$_3$ complexed to a phospine ligand such as 2-(tert-butyl$_2$-phosphino)biphenyl; Pd$_2$(dba)$_3$ complexed to 9,9-Dimethyl-4,5-bis(diphenyl-phosphino)xanthene (Xantphos); Pd(dba)$_2$ complexed to P(t-Bu)$_3$; Pd(OAc)$_2$ complexed to (o-biphenyl)P(t-Bu)$_2$; and Pd$_2$(dba)$_3$ complexed to (o-biphenyl)P(t-Cy)$_2$. Copper catalysts which are useful in the above coupling reaction include those catalysts in which the copper is complexed with one or more ligands, including but not limited to CuI/ethylene glycol complex; CuBr/DBU complex, Cu(PPh$_3$)Br; and Cu(PPh$_3$)Br additionally complexed to 1,10-phenanthroline or neocuproine (e.g., Cu(phen) (PPh$_3$)Br and Cu(neocup)(PPh$_3$)Br, respectively), and the like.

Bases which are useful in the above coupling reaction include but are not limited to potassium carbonate, sodium carbonate, cesium carbonate, cesium hydroxide, sodium tert-butoxide, potassium tert-butoxide, potassium phenoxide, triethylamine, and the like, or mixtures thereof. Solvents may be used in such coupling reactions including but not limited to toluene, xylenes, diglyme, tetrahydrofuran, dimethylethyleneglycol, DMF, NMP, and the like, or mixtures thereof. This reaction can be carried out at a temperature of 50 to 90° C. In the above Scheme D, particularly preferred reaction conditions include X being I, Pd$_2$(dba)$_3$ as a catalyst complexed to Xantphos, CsOH as a base, NMP as a solvent, and carried out at 80° C.

The final reaction step in Scheme D above is carried out by reacting a compound of formula 12 with an activated substituent X. This reaction can be carried out using a suitable base and a suitable solvent at room temperature. For example, KOH can be used as a base, and NMP can be used as a solvent. KOH can be charged as a solid or as an as an aqueous solution (e.g. 45% aqueous solution), which is useful when this reaction is carried out at large scale. Preferably, the activated substituent X is I.

EXAMPLES

In the examples described below, unless otherwise indicated, all temperatures in the following description are in degrees Celsius (° C.) and all parts and percentages are by weight, unless indicated otherwise.

Various starting materials and other reagents were purchased from commercial suppliers, such as Aldrich Chemical Company, Regis Chemical Company, and SAI Lifesciences, EM Science, and used without further purification, unless otherwise indicated.

The reactions set forth below were performed under a positive pressure of nitrogen, argon or with a drying tube, at ambient temperature (unless otherwise stated), in anhydrous solvents. Analytical thin-layer chromatography was performed on glass-backed silica gel 60° F. 254 plates (Analtech (0.25 mm)) and eluted with the appropriate solvent ratios (v/v). The reactions were assayed by high-pressure liquid chromatography (HPLC) or thin-layer chromatography (TLC) and terminated as judged by the consumption of starting material. The TLC plates were visualized by UV, phosphomolybdic acid stain, or iodine stain.

$^1$H-NMR spectra were recorded on a Bruker instrument operating at 300 MHz and $^{13}$C-NMR spectra were recorded at 75 MHz. NMR spectra are obtained as DMSO-d$_6$ or CDCl$_3$ solutions (reported in ppm), using chloroform as the reference standard (7.25 ppm and 77.00 ppm) or DMSO-d$_6$ (2.50 ppm and 39.52 ppm). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as CDCl$_3$ solutions, and when reported are in wave numbers (cm$^{-1}$). The mass spectra were obtained using LC/MS or APCI. All melting points are uncorrected.

All final products had greater than 95% purity (by HPLC at wavelengths of 220 nm and 254 nm).

The examples and preparations provided below further illustrate and exemplify the methods of the present invention. It is to be understood that the scope of the present invention is not limited in any way by the scope of the following examples.

Example 1

Preparation of 6-[2-(methylcarbamoyl)phenylsulfanyl]-3-E-[2-(Pyridine-2-yl)ethenyl]indazole

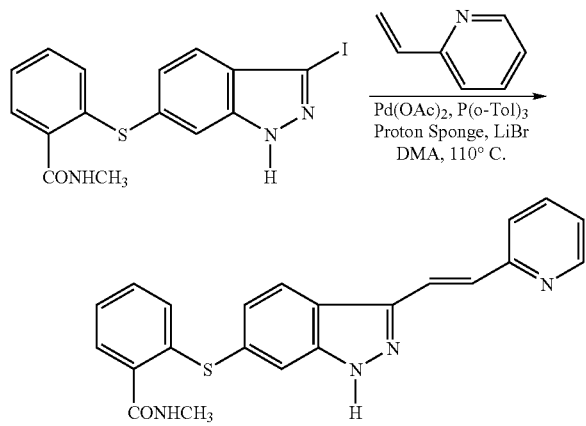

2-(3-Iodo-1H-indazol-6-ylsulfanyl)-N-methyl-benzamide (239.19 g), 2-vinylpyridine (75.7 mL, 702 Mmol), Pd(OAc)$_2$ (6.56 g), P(o-Tol)$_3$ (23.12 g), Proton Sponge (187.82 g), LiBr (314.59 g), and DMA (3.1 L, 3.5 mL/g) were added to a 5 L 3-neck flask, equipped with a mechanical stirrer and a temperature probe. The mixture was degassed three times by alternately connecting to house vacuum and nitrogen. The mixture was then heated to 110° C. in one hour and the temperature was maintained at 110° C. for 24 hours, at which time all of the 2-(3-Iodo-1H-indazol-6-ylsulfanyl)-N-methyl-benzamide was consumed (HPLC). After cooling, the mixture was transferred to a 22 L extractor and followed by the addition of 5.5 L of CH$_2$Cl$_2$, 5.5 L of water and 275 mL of 37% aqueous HCl. After agitation and partitioning, the organic phase was extracted twice with 2.0 L of water and 100 mL of 37% HCl. At this stage, the organic phase (HPLC) did not contain any significant amount of the final product (HPLC), and was discarded. The combined aqueous layers were treated with 2.2 L of toluene, followed by the addition of 1.05 L of 28% NH$_4$OH over 45 minutes of time (via addition funnel). A thick precipitate formed at this stage. The resulting mixture was allowed to stir for approximately 48 hours. The mixture was then filtered and sucked dry. The cake was triturated with 3.5 L of toluene, stirred overnight, filtered and sucked dry. The cake was then transferred to a glass dish and dried at 50° C. under house vacuum overnight to afford 160.20 g of the final product.

$^1$H NMR, 300 MHz, (DMSO-D6), ppm; 13.35 (1 H, s), 8.61 (1 H, d, J=3.8 Hz), 8.39 (1 H, q, J=4.4 Hz), 8.21 (1 H, d, J=8.8 Hz), 7.96 (1 H, d, J=16.4 Hz), 7.85-7.76 (1 H, m), 7.66 (1 H, d, J=7.8 Hz), 7.61 (1 H, s), 7.58 (1 H, d, J=16.5 Hz), 7.50 (1 H, dd, J=5.7 Hz), 7.36-7.23 (3 H, m), 7.192 (1 H, dd, J=8.4, 1.2 Hz), 7.05 (1 H, dd, J=7.5, 1.5 Hz), 2.78 (3 H, d, J=4.5 Hz).

Example 2

Preparation of 2-(3-Iodo-1H-indazol-6-ylsulfanyl)-N-methyl-benzamide

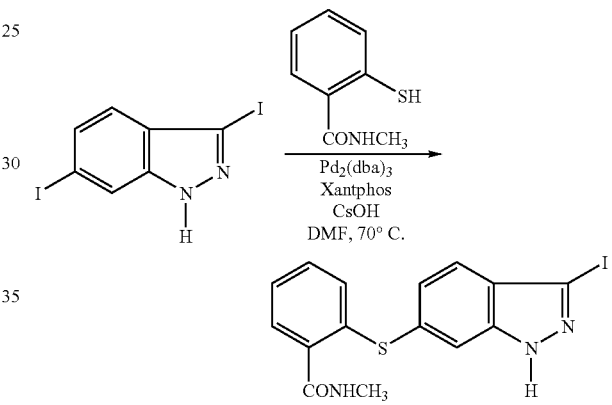

3,6-diiodoindazole (250.00 g), 2-mercapto-N-methylbenzamide (118.48 g), Pd$_2$(dba)$_3$ (9.28 g), Xantphos (11.73 g), DMF (2.5 L, 10 mL/g), followed by CsOH were added sequentially to a 5 L four-neck flask equipped with a mechanical stirrer and a temperature probe. The reaction mixture was then stirred. The dark mixture was degassed three times by alternately connecting to house vacuum and then nitrogen. The mixture was heated to 70° C. over a period of 30 minutes and maintained at the same temperature for fours, at which time HPLC of the aliquot indicated that the 3,6-diiodoindazole was less than 3%. After cooling, the mixture was poured into a mixture of 7.5 L of water, 1.25 L of toluene and 1.25 L of CH$_2$Cl$_2$ in a 22 L extractor. The mixture was allowed to stir at ambient temperature overnight. A thick precipitate formed overnight. The mixture was filtered and the cake was sucked dry. The cake was further dried at 35° C. under house vacuum for six hours to afford 216 g of the final product. The mother liquor was thenextracted with 1.5 L of EtOAc. After partitioning, the aqueous layer was discarded. The organic layer was washed twice each with 2 L of water and concentrated. The residue was treated with 250 mL of CH$_2$Cl$_2$ and stored overnight. A thick precipitate formed overnight. The mixture was filtered and the cake was sucked dry. The cake was dried at 35° C. under house vacuum overnight to afford 24.71 g of the final product. The combined yield was 241 g of the final product. The material showed satisfactory purity and was used in the next step without further purification.

¹H NMR 300 MHz, DMSO ppm: 13.53 (s, 1H), 8.35 (q, J=4.7 Hz, 1H), 7.56 (s, 1H), 7.51-7.40 (m, 2H), 7.36-7.23 (m, 3H), 7.13 (dd, J=8.5, 1.3 Hz, 1H), 7.06-7.01 (m, 1H), 2.76 (d, J=4.7 Hz, 3H).

Example 3

Preparation of 3,6-diodoindazole

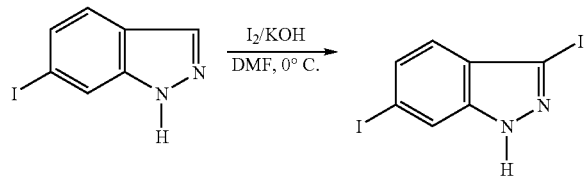

An aqueous solution of NaHSO₃ was prepared by adding 13.6 g of solid NaHSO₃ into 250 mL of DI water with strong stirring. 6-iodoindazole (30.0 g), followed by DMF (60 mL) were added to a 500 mL three-neck flask that was fitted with a mechanical stirrer, a temperature probe, and a 100 mL dropping funnel. After the stirring had begun, the flask was immersed in an ice/water bath. After 30 mintues, KOH was added in one portion, and the resulting mixture was stirred for an additional 30 minutes. A solution of 54.3g of I₂ in 55 mL of DMF (total volume was 71 mL) was added to the dropping funnel and the run-in started. After 30 minutes, 42 mL of the solution had been added to the reaction mixture. The addition was stopped and an aliquot sample was taken and analyzed with HPLC (TFASH method), which indicated that there was still 6-iodoindazole present. After an additional 10 mL of the iodine/DMF solution was added, the second aliquot sample showed that all the starting 6-iodoindazle was consumed. A solution of 13.6 g of NaHSO₃ in DI water was added slowly to the reaction mixture. At this stage the dark solution became a yellow suspension. After stirring for one hour, the mixture was filtered and the cake was washed with 200 mL of water and 200 mL of hexanes. The cake was sucked dry and further dried in a vacuum oven (25 inch vacuum/60° C.) for 18 hours to afford 38.60 g of the final product as a tan solid.

¹H NMR 300MHz, DMSO ppm: 7.96 (s, 1H), 7.46 (d, J=8.4 Hz, 1H), 7.24 (d, J=8.4 Hz, 1H), 3.33 (s, 1H).

Example 4

Final Deprotection Step to Produce 6-[2-(methyl-carbamoyl)phenylsulfanyl]-3-E-[2-(pyridine-2-yl)ethenyl]indazole

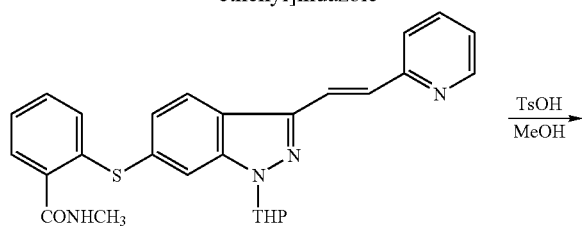

N-1 THP 6-[2-(methylcarbamoyl)phenylsulfanyl]-3-E-[2-(pyridine-2-yl)ethenyl]indazole (355 g) was suspended in 2,485 mL of methanol, after which p-toluenesulfonic acid monohydrate (718 g) was added. The mixture was then heated to 65° C. (hard reflux) for 4 hours under argon while the reaction was monitored by HPLC (gluco method). Heating continued until less than 1% of the N-1 THP protected starting material persisted. The heating was then removed and the reaction was cooled to room temperature. The solid was filtered and the wet cake was washed with methanol (2 volumes, 710 mL) then the solids were rinsed with ethyl acetate (2 volumes, 710 mL). The wet cake was transferred to a reactor containing sodium bicarbonate (126.84 g), deionized water (1800 mL), and ethyl acetate (975 mL), which was then stirred for 2 hours at 20° C. The solids were filtered and washed with 5 volumes of deionized water (1800 mL), then with 2 volumes of ethyl acetate (760 mL), and then dried in a vacuum oven at 40° C. for 16 hours. The isolated yield for the reaction was 92.5% (274 g). The isolated material was identified as crystalline Form III free base (0.5 ethyl acetate solvate).

¹H NMR, 300 MHz, (DMSO-D6), ppm; 13.35 (1 H, s), 8.60 (1 H, d, J=3.8 Hz), 8.39 (1 H, m), 8.23 (1 H, d, J=8.5 Hz), 7.95 (1 H, d, J=16.4 Hz), 7.82 (1 H, ddd, J=7.7, 7.6, 1.8 Hz), 7.67 (1 H, d, J=7.8 Hz), 7.60 (1 H, s), 7.57 (1 H, d, J=16.4 Hz), 7.49 (1 H, dd, J=7.1, 1.6 Hz), 7.35-7.26 (3 H, m), 7.19 (1 H, d, J=8.4 Hz), 7.04 (1 H, d, J=7.8 Hz), 2.77 (3 H, d, J=4.6 Hz).

¹³C NMR, 75 MHz, (DMSO-D6) ppm: 168.23, 155.18, 149.81, 142.35, 142.22, 137.31, 136.00, 132.89, 130.64, 130.36, 129.51, 128.14, 126.50, 125.93, 124.08, 123.01, 122.85, 122.12, 120.642, 115.08, 26.45.

Example 5

Preparation of 6-[2-(methylcarbamoyl)phenylsulfanyl]-3-E-[2pyridine-2-yl)ethenyl]indazole Using the Tetrahydropyranyl Protecting Group

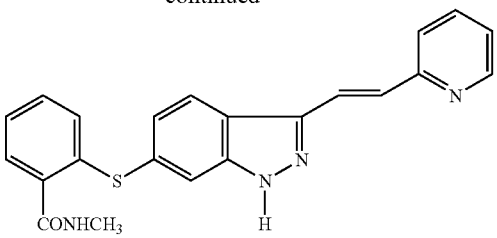

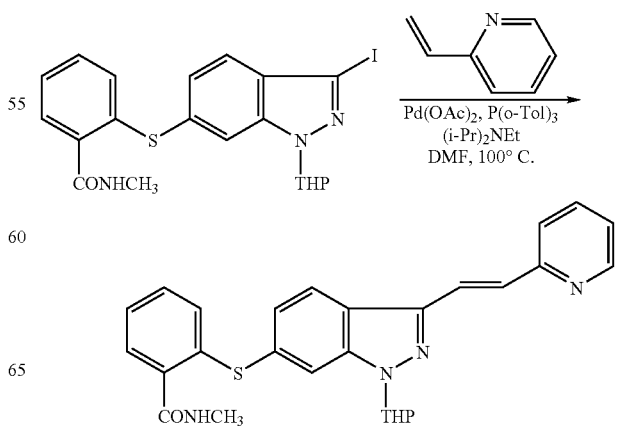

N-1 THP 2-(3-Iodo-1H-indazol-6-ylsulfanyl)-N-methyl-benzamide (21.77 g), 2-vinylpyridine (5.92 mL, 54.9 Mmol), Pd(OAc)₂ (0.96 g), P(o-Tol)₃ (3.42 g), (i-Pr)₂NEt (11.3 mL, 64.9 Mmol), and N,N-dimethylformamide (550 mL) were added to a 1 L 3-neck flask, equipped with a mechanical stirrer and a temperature probe. The mixture was then degassed three times by alternately connecting to house vacuum and nitrogen. The mixture was heated to 100° C. and the temperature was maintained at 100° C. overnight, at which time all the starting material was consumed (HPLC). After cooling, the mixture was poured into 800 mL of saturated NaHCO₃ and 400 mL of EtOAc was added. The mixture was stirred for half an hour at which time a thick precipitate formed. The solid was filtered off and the filtrate was allowed to partition. After partitioning, the aqueous layer was extracted twice with 300 mL of EtOAc. The combined organic layers were washed twice with water, dried over MgSO₄ and concentrated. The residue crystallized on standing at room temperature. The solid was treated with 20 mL of EtOAc and filtered. The cake was allowed to air-dry overnight and afforded 17.66 g of the final product.

Example 6

Preparation of N-1 THP-protected 2-(3-Iodo-1H-indazol-6-ylsulfanyl)-N-methyl-benzamide

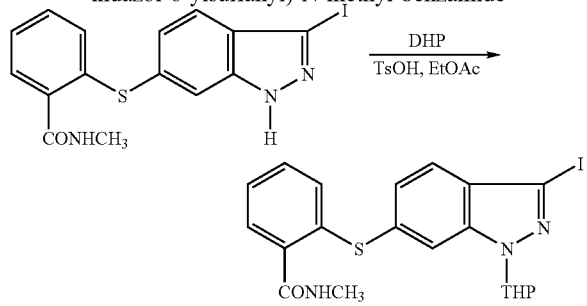

A mixture of 2-(3-Iodo-1H-indazol-6-ylsulfanyl)-N-methyl-benzamide (24.65 g), dihydropyran (5.50 mL, 60.3 Mmol), and TsOH.H₂O (1.146 g) in 600 mL of EtOAc was heated at 60° C. overnight. After cooling, the mixture was diluted with 500 mL of EtOAc, washed with NaHCO₃ (200 mL), dried over MgSO₄ and then concentrated in vacuo. The residue was pre-adsorbed onto silica gel and subjected to flash chromatography, using hexanes/EtOAc (2:1, 1:1, 1:2, 1:3) to yield 21.77 g of the final product.

¹H NMR, 300 MHz, DMSO δ 8.35 (q, J=4.5 Hz, 1H), 7.92 (s, 1H), 7.53-7.41 (m, 2H), 7.34-7.22 (m, 2H), 7.17 (dd, J=8.4 1.5 Hz, 1H), 7.97 (dd, J=7.1, 1.9 Hz, 1H), 5.87 (dd, J=9.6, 2.1 Hz, 1H), 3.93-3.79 (m, 1H), 3.79-3.65 (m, 1H), 2.77 (d, J=4.8 Hz, 3H), 2.44-2.23 (m, 1H), 2.08-1.89 (m, 2H), 1.82-1.62 (m, 1H), 1.62-1.48 (m, 2H).

Example 7
Preparation of 6-[2-methylcarbamoyl)phenylsulfanyl]-3-E-[2-pyridine-2-yl)ethenyl]indazole Using the tert-butoxycarbonyl Protecting Group

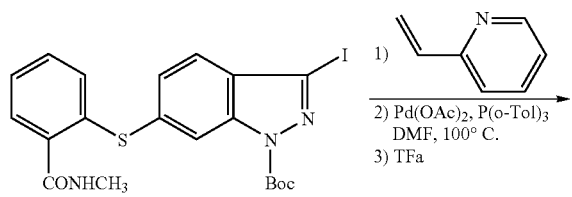

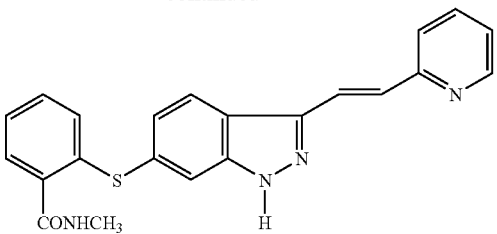

N-1 Boc 2-(3-Iodo-1H-indazol-6-ylsulfanyl)-N-methyl-benzamide (510 mg), and 2-vinylpyridine (0.14 mL, 1.3 Mmol) were added to a 100 mL 3-neck flask, equipped with a stirring bar and a temperature probe. The mixture was then degassed three times by alternately connecting to house vacuum and nitrogen. The mixture was allowed to stir for two hours, after which an aliquot indicated that only the starting material was present (HPLC). Initially, Pd[P(t-Bu)₃]₂ was used as a catalyst (9.28 g), along with 20 mL of DMF, and 124 mL of Cy₂NMe (711 Mmol) at room temperature for 2 hours, but the reaction did not work. Subsequently, it was found that when Pd(OAc)₂ was used as the catalyst, along with P(o-Tol)₃, the reaction worked. However, the role of the Pd[P(t-Bu)₃]₂ catalyst in the overall reaction could not be excluded. Accordingly, 22 mg of Pd(OAc)₂ and 91 mg of P(o-Tol)₃ were then added to the flask and the mixture was degassed again by alternately connecting to house vacuum and nitrogen three times. The mixture was heated to 100° C. and the temperature was maintained at 100° C. overnight, at which time all the starting material was consumed (HPLC). TFA (1.0 mL, 13.0 Mmol) was added to remove the Boc protecting group. After cooling, the mixture was poured into a mixture of 100 mL of water and 100 mL of EtOAc. After partitioning, the aqueous layer was extracted twice with 50 mL of EtOAc. The combined organic layers were washed twice with water, dried over MgSO₄ and concentrated. The residue was pre-adsorbed onto silica and subjected to gradient flash chromatography (Hexanes/EtOAc, 1:3, 1:4, EtOAc, EtOAc/MeOH, 100:1, 50/1) to yield 155 mg of the final product.

Example 8

Preparation of N-1 Boc 2-(3-Iodo-1H-indazol-6-ylsulfanyl)-N-methyl-benzamide

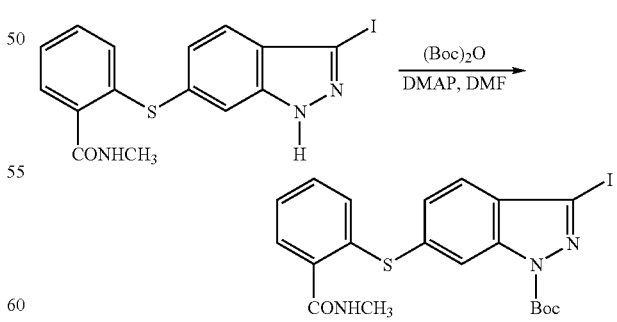

(Boc)₂O (1.18 g) was added in small portions to a solution of 2-(3-Iodo-1H-indazol-6-ylsulfanyl)-N-methyl-benzamide (2.20 g), dimethylamino pyridine (66 mg), and N,N-dimethylfonmamide (22 mL), which was chilled in an ice-water bath. At the completion of the addition, HPLC of the aliquot indicated that all the 2-(3-Iodo-1H-indazol-6-ylsulfanyl)-N-methyl-benzamide was consumed. The reaction mixture was poured into a mixture of 100 mL of EtOAc and 100 mL of water. After partitioning, the aqueous layer was extracted two more times with 50 mL of EtOAc. The combined organic layers were washed twice with water, dried over MgSO₄ and concentrated. The residue was chromatographed using Hexanes/EtOAc (1:1, 1:2, 1:4, 0:1) to afford 1.35 g of the final product.

¹H NMR, 300 MHz, CDCl₃ δ 8.06 (s, 1H), 7.68-7.56 (m, 1H), 7.43-7.20 (m, 5H), 6.60 (d, J=4.2 Hz, 1H), 2.92 (d, J=5.1 Hz, 3H), 1.62 (s, 9H).

Example 9

Preparation of 6-[2-methylcarbamoyl)phenylsulfanyl]-3-[2-pyridine-2-yl)ethynyl]indazole

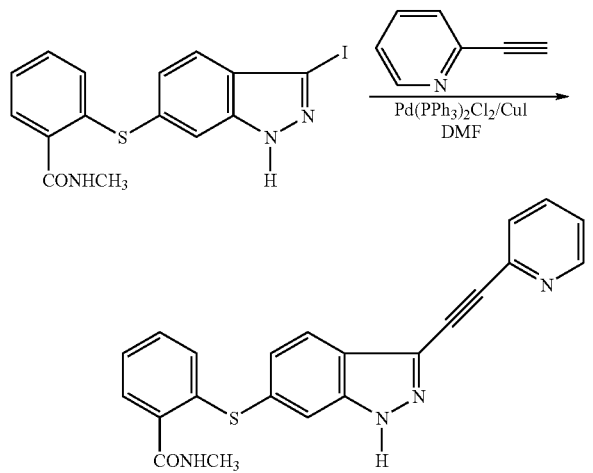

2-(3-Iodo-1H-indazol-6-ylsulfanyl)-N-methyl-benzamide (2.30 g), 2-ethynylpyridine (0.25 mL), Pd(PPh₃)₂Cl₂ (128 mg), CuI (64 mg), (i-Pr)₂NEt (0.50 mL), and N,N-dimethylformamide (15 mL) were added to a 50 mL 3-neck flask, equipped with a stirring bar and a temperature probe. The mixture was degassed by alternately connecting to house vacuum and nitrogen three times, and heated at 66° C. for one hour. To the warm mixture was added 0.16 mL of 2-ethynylpyridine and 0.30 mL of (i-Pr)₂NEt. The resulting mixture was allowed to stir at 66° C. overnight, at which time HPLC indicated that all the starting material was consumed. After cooling, the mixture was diluted with 100 mL of dichloromethane and washed with water. To the organic layer was added 10 g of silica and agitated vigorously. The mixture was then filtered and the filtrate was discarded. The silica was then washed with tetrahydrofuran/dichloromethane (discarded) and followed by pure tetrahydrofuran. The tetrahydrofuran solution was concentrated in vacuo to yield 0.95 g of the final product.

¹H NMR, 300 MHz, DMSO δ 13.66 (s, 1H), 8.65 (d, J=4.7 Hz, 1H), 8.34 (q, J=4.9 Hz, 1H), 7.94-7.81 (m, 2H), 7.76 (d, j+7.9 Hz, 1H), 7.63 (s, 1H), 7.53-7.41 (m, 2H), 7.38-7.26 (m, 2H), 7.22 (dd, J=8.7, 1.5 Hz, 1H), 7.08 (dd, J=7.0, 2.1 Hz, 1H), 2.76 (d, J=4.5 Hz, 3H).

Example 10

Preparation of 6-[2-(methylcarbamoyl)phenylsulfanyl]-3-Z-[2-(pyridine-2-yl)ethenyl]indazole

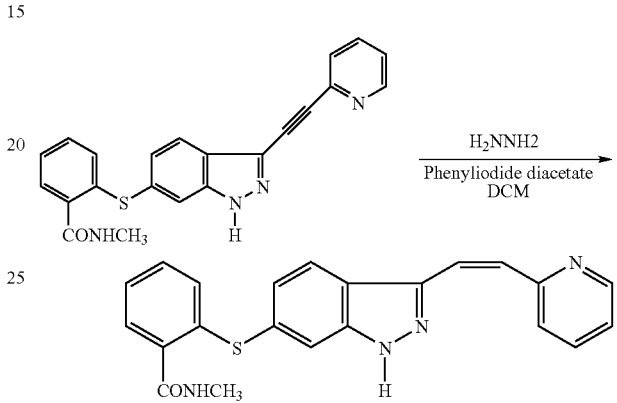

To a 100 mL 3-neck flask containing a solution of 0.95 g of 6-[2-(methylcarbamoyl)phenylsulfanyl]-3-[2-(pyridine-2-yl)ethynyl]indazole was added 2.5 g of phenyliodide diacetate followed by 1.0 mL of H₂NNH₂.H₂O. After the bubbling had settled, more phenyliodide diacetate and H₂NNH₂.H₂O were added in small portions, until LC/MS indicated the disappearance of 6-[2-(methylcarbamoyl)phenylsulfanyl]-3-[2-(pyridine-2-yl)ethynyl]indazole and the formation of 6-[2-(methylcarbamoyl)phenylsulfanyl]-3-Z-[2-(pyridine-2-yl)ethenyl]indazole.

¹H NMR, 500 MHz, CD₂Cl₂ δ 8.89 (d, J=2.4 Hz, 1H), 7.90 (s, 1H), 7.86-7.90 (m, 1H), 7.82 (d, J=8.8 Hz, 1H) 7.56 (d, J=6.6 Hz, 1H), 7.51 (d, J=8.3 Hz, 1H), 7.35-7.40 (m, 1H), 7.23-7.30 (m, 2H), 7.21 (d, J=6.6 Hz, 1H), 7.15 (d, J=8.3 Hz, 1H), 7.04 (d, J=13.3 Hz, 1H), 6.70 (d, J=12.6 Hz, 1H), 6.30 (s, 1H), 2.92 (d, J=4.5 Hz, 1H).

Example 11

Palladium Removal and Polymorph Control of 6-[2-(methylcarbamoyl)phenylsulfanyl]-3-E-[2-(pyridine-2-yl)ethenyl]indazole

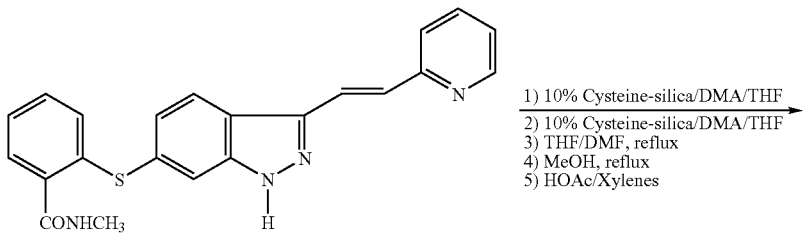

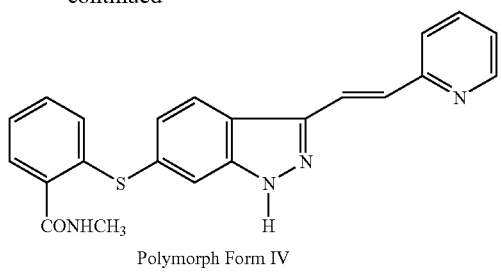

Polymorph Form IV

To a 12 L 3-neck flask, equipped with a mechanical stirrer, was added 160.20 g of 6-[2-(methylcarbamoyl)phenylsulfanyl]-3-E-[2-(pyridine-2-yl)ethenyl]indazole and 1.6 L of DMA and 1.6 L of THF. After stirring for 20 minutes, the mixture became homogeneous. To the clear solution was added 800.99 g of 10% cysteine-silica and the resulting mixture was allowed to stir at room temperature overnight.

The mixture was filtered through a medium sintered glass fritted funnel, and the cake was washed with a solution of 500 mL of DMA and 500 mL of THF. The cake was further washed with 2.0 L of THF and the filtrate was collected into a separate flask. The volatile parts in the latter filtrate were removed in vacuo and the residue was combined with the main filtrate. The combined filtrate was recharged back into the 12 L flask, followed by 800 g of 10% cysteine-silica. The flask was equipped with a mechanical stirrer and stirred over the weekend at room temperature.

The mixture was then filtered through a medium sintered glass fritted funnel and the silica was washed with a mixture of solvents of 500 mL of DMA and 500 mL of THF, followed by 3.0 L of THF. The volatile parts in the filtrate were removed in vacuo and the remaining solution was transferred to a 22 L 3-neck flask and treated with 12 L of water (added over a 20 minute period of time), a thick precipitate formed at this stage. After stirring overnight, the mixture was filtered and the cake was washed with 2.0 L of water and sucked dry.

The cake was charged to a 5 L 3-neck flask, followed by 1.6 L of THF and 160 mL of DMF. The flask was equipped with a mechanical stirrer, a reflux condenser and the mixture was heated at reflux for 8 hours. After cooling overnight, the mixture was filtered through sharkskin filter paper and sucked dry.

The cake was charged to a 5 L 3-neck flask and 1.6 L of MeOH was added. The flask was equipped with a mechanical stirrer, a water condenser and the contents were heated at reflux for 6 hours. After cooling overnight, the mixture was filtered through sharkskin filter paper and sucked dry.

The cake was dissolved into 1.6 L of HOAc with the assistance of gentle heating in the water bath of a rotary evaporator. The solution was filtered through #3 filter paper and the total volume of the filtrate was reduced to ~500 mL in volume on the rotary evaporator at 60° C./60 mmHg. At this stage, the bulk of the mixture remained a yellow solution and a small amount of precipitate formed. To the flask was charged 500 mL of xylenes (precipitate formed) and the total volume was reduced to ~500 mL in volume on the rotary evaporator at 60° C./60 mmHg. The process was repeated two more times. After cooling, the mixture was filtered, the cake was washed with 500 mL of xylenes and sucked dry. The cake was transferred to a glass dish and further dried at 80° C./27 inch vacuum overnight.

The cake was off-white in color and weighed 108.38 g. X-ray powder diffraction analysis indicated that a crystalline form was present, which was characterized as Form IV by a powder X-ray diffraction pattern comprising peaks at the following approximate diffraction angles (2θ): 8.9, 12.0, 14.6, 15.2, 15.7, 17.8, 19.2, 20.5, 21.6, 23.2, 24.2, 24.8, 26.2, and 27.5.

Example 12

Preparation of 2-(3-Iodo-1H-indazol-6-ylsulfanyl)-N-methyl-benzamide

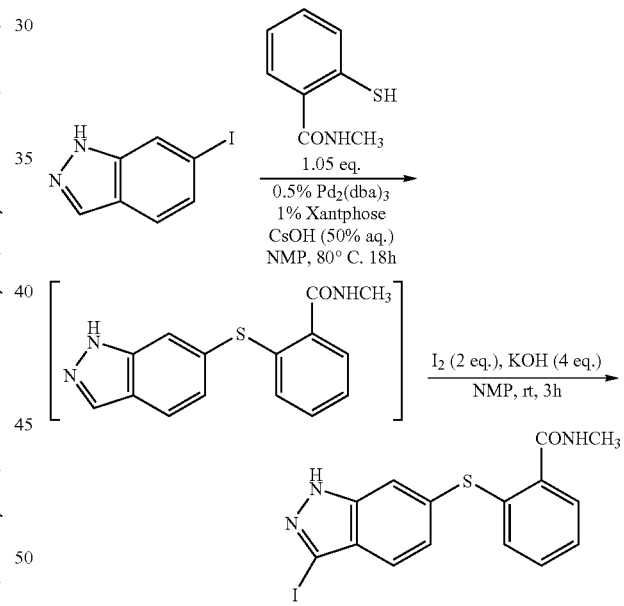

A 5 L three neck flask was equipped with a mechanical stirrer, a temperature probe, and a $N_2$ inlet. The flask was charged with 6-iodoindazole (200 g) followed by 2-mercapto-N-methylbenzamide (144 g), $Pd_2(dba)_3$ (3.75 g), Xantphos (4.74 g), NMP (1.2 L), and 50% aqueous CsOH solution (150 mL) in that order. Stirring was then commenced. The dark reaction mixture was degassed three times by alternately connecting to house vacuum and nitrogen. The mixture was heated to 80° C. over a period of half an hour and maintained at the same temperature for 18 hours. The reaction was monitored by HPLC. It was noted that heating may be discontinued when the amount of 6-diiodo-indazole is <3%. The reaction mixture was allowed to cool to room temperature.

An aqueous solution of NaHSO₃ was prepared by adding 90 g of solid NaHSO₃ into 1.5 L of deionized water with strong stirring. This solution was then set aside until the reaction quench step as described below. The reaction mixture in the 5 L flask was chilled in an ice-water bath until an internal temperature of 0.9° C. was reached. KOH (183 g) was then charged in a single portion and the resulting mixture was allowed to stir for half an hour in ice-water bath (slight exotherm, highest point 4.0° C.). Iodine (417 g) was dissolved in NMP (420 mL) in a separate flask with stirring. Once complete dissolution of iodine was been confirmed, the dark mixture was charged to a 1 L addition funnel.

The iodine/NMP solution was then added dropwise over 1 h to the reaction mixture. (Note: the addition is exothermic and the internal reaction temperature must therefore be controlled via external cooling in addition to the controlled addition rate; the internal temperature should be kept between 0° C. and 16.8° C.). Upon complete addition the final temperature was 14.5° C.

The flask was then taken out of the bath and the internal temperature reached 21.1° C. in 70 min. The mixture was allowed to stir at room temperature for three hours, at which time, analysis of an aliquot sample indicated the reaction was complete (<3% left). Upon confirmation of reaction completion (HPLC), the flask was re-immersed in the ice-water bath. The aqueous NaHSO₃ solution prepared as described previously was added slowly over 40 minutes from an addition funnel. (Note: this addition is exothermic and the internal reaction temperature must therefore be controlled via external cooling in addition to the controlled addition rate; the internal temperature should be kept below 15.7° C.). Upon complete addition the reaction was a slurry of light yellow solids. The mixture was allowed to stir at ambient temperature overnight.

The solid product was collected by filtration. The wet cake was recharged back into the 5 L flask and the funnel was rinsed with 1.5 L of water, and the rinses were also charged into the 5 L flask. The mixture was stirred for one hour and filtered. The wet cake was recharged back to the 5 L flask, and the funnel was rinsed with 1.5 L of methanol, and the rinses were also charged into the 5 L flask. The mixture was heated at 45° C. for two hours, then allowed to cool. The mixture was filtered and the cake was washed with 500 mL of MeOH, and sucked dry. The product (cake) was placed in a vacuum oven at 60° C. for 18 h to afford 317 g of 2-(3-Iodo-1H-indazol-6-ylsulfanyl)-N-methyl-benzamide.

Example 13

Preparation of 6-[2-methylcarbamoyl)phenylsulfanyl]-3-E-[2-(pyridine-2-yl)ethenyl]indazole

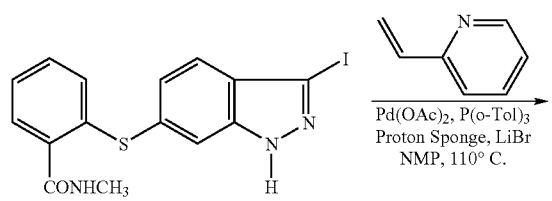

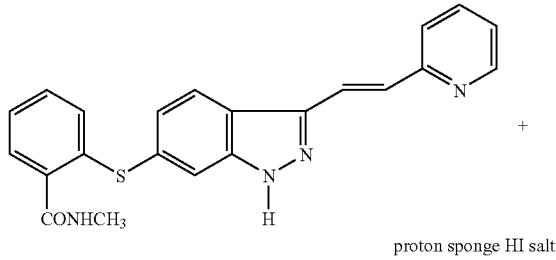

proton sponge HI salt

A 3 L 3-neck flask was equipped with a mechanical stirrer, temperature probe, and a nitrogen inlet. 2-(3-Iodo-1H-indazol-6-ylsulfanyl)-N-methyl-benzamide (200 g), as prepared in Example 12, was charged to the flask followed by Pd(OAc)₂ (5.48 g), P(o-tol)₃ (19.3 g), proton sponge (104.7 g) and NMP (1.0 L). Note this initial mixing was slightly endothermic, with the temperature dropping from 22.8° C. to 20.9° C. Also note, it is possible to use less Pd(OAc)₂ (e.g. as little as 1 to 2%) if Xantphos is also added. In addition, it is possible to replace proton sponge as the base and instead use bases such as N-methyl-piperidine or N,N-diisopropylethylamine (Hunig's base).

After stirring had started, LiBr (262 g) was added. This addition was exothermic, the temperature rose from 20.9° C. to 68° C. in 15 min, then began to fall. 2-vinyl pyridine (69 mL) was then added. The mixture was degassed three times by alternately connecting to house vacuum and nitrogen. The mixture was heated at 110° C. over one hour and the temperature was maintained at 110° C. for 18 h. The reaction was monitored by HPLC until all of the 2-(3-Iodo-1H-indazol-6-ylsulfanyl)-N-methyl-benzamide was was consumed. Heating was then discontinued and the reaction was allowed to cool to room temperature.

In a separate operation, 250 mL of concentrated HCl (0.25 L) was carefully added to 2750 mL deionized water to prepare the required 3.0 L of 1.0 N hydrochloric acid solution to be used in the next step. To the reaction mixture was added 1 N aqueous HCl (2L) while continuing to stir. Note, the HCl addition is mildly exothermic.

Methyl-isobutyl ketone (MIBK, 2L) was then added and the mixture was agitated vigorously (300-400 RPM) for 2 hours. During this partitioning step, some solids were formed. The solids were removed via filtration through a 1" pad of celite. The filter cake was washed with both 1N HCl (200 mL) and MIBK (200 mL). Note, this filtration may possibly be slow on scale-up. At present scale, ~2.5+ L passed through 2 L sinterglass funnel in less than 4 minutes. The collected solids were mostly proton sponge and dimeric impurity by HPLC. As standard precaution, the identity of the solids should be confirmed by HPLC before discarding.

The filtrate was agitated via vigorous mechanical stirring and then allowed to separate into organic (upper) and aqueous (lower) layers. The lower aqueous layer was drained (~3.6 L) and the organic layer was extracted twice with 1 N HCl (500 mL then 300 mL). The acidic aqueous extracts were pooled and washed once with MIBK (1 L). The final volume for the lower aqueous layer was ~4.3 L; upper MIBK layer volume was ~1.1 L. Based on subsequent experiments it is recommended that further agitation should not be carried out since phase mixing is accomplished as described previously. Further agitation requires more time to allow for phase re-separation and is not necessary. The initial MIBK extract may be very close in color to the aqueous phase and difficult to distinguish; measured volumes are given above.

To the combined aqueous layer was added toluene (1 L) and the mixture was transferred to a reaction flask with an overhead stirrer and pH meter. The mixture was stirred rapidly (400 rpm) while 28% NH$_4$OH (300 mL) was slowly added over 20 to 30 minutes via addition funnel. Since the target pH is 9, extra reagent should be on hand because slightly more or less base may need to be added to reach the desired pH endpoint. Slow addition of NH$_4$OH was necessary to prevent formation of gummy (unfilterable) solids; toluene helped to prevent formation of this gummy product by dissolving proton sponge as it was deposited during basification. Solids were then collected by filtration. The filter cake was washed with water (1 L) and toluene (400 mL). Note, on 2L sintered-glass Buchner funnel, initial filtration and washes (total volume ~7.5L) were completed within 9 minutes. The cake was then transferred to a glass dish and dried at 60° C. under house vacuum for 24 hours to afford 148.2 g (78% yield) of crude 6-[2-(methylcarbamoyl)phenylsulfanyl]-3-E-[2-(pyridine-2-yl)ethenyl]indazole as a light orange solid.

Note, the reaction was monitored via HPLC (TFASH method, details contained herein). Sample preparation was as follows: 1 drop of the reaction mixture was diluted with 1 mL of methanol and 1 mL of 80/20 0.1N HCl/ACN was added; sample shaken. Product assay was carried out as above with 0.5 mg sample. Typical purity was 83-87%. The product contained NMP, which was visible by $^1$H NMR.

Example 14

Palladium Removal cloudy. After a few minutes, a precipitate formed. Stirring (250 RPM or less, moderate stir rate) was continued for 18 hours. Note, after MeOH was added, granulation was carried out for 18 h. Use of a shorter granulation time has been shown to reduce yield. Use of a longer granulation time does not increase yield but may be carried out without any adverse effect.

The granular solid was then collected by filtration. The solids were washed with 105 mL (3 volumes) of MeOH. The solids were pulled dry via suction on a filter. The cake was transferred to a glass dish and dried at 65° C. under house vacuum for 18 hours to afford 26 g of 6-[2-(methylcarbamoyl)phenylsulfanyl]-3-E-[2-(pyridine-2-yl)ethenyl]indazole as an off-white, granular solid (74% recovery by weight; purity-corrected recovery is 89%). The product was 97+% pure by HPLC (TFASH method) but contained DIPHOS, visible by NMR that was removed in the next steps. The product thus obtained contained 16 ppm residual palladium metal (the original Pd content before treatment was 1189 ppm).

A portion of the product (21.2 g) was charged to a flask and tetrahydrofuran (210 mL, 10 mL/g) was added under an atmosphere of nitrogen. The mixture was heated to 65° C., under ~250 rpm stirring, for 15 h. The mixture remained a suspension of solids throughout the reslurry. The mixture was cooled to room temperature and stirred for 3 h. The solids were collected by filtration, washed with 42 mL (2 volumes) of THF and then were pulled dry on the filter via suction. Note, the small wash volume of THF was used because the THF appeared to wash some product into the filtrate. It is recommended to not use more than 2 volumes for the wash or for rinsing forward material.

The solids were then dried in a vacuum oven at 65° C. for 18 h. The resulting white solid weighed 16 g (76% recovery

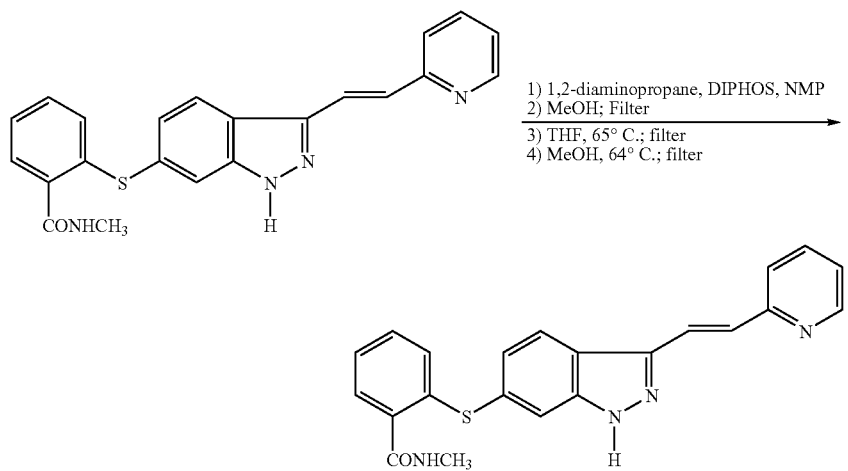

To a 250 mL round bottom flask under a nitrogen atmosphere was charged crude 6-[2-(methylcarbamoyl)phenylsulfanyl]-3-E-[2-(pyridine-2-yl)ethenyl]indazole (35 g)—as prepared in Example 13—DIPHOS, NMP (175 mL) and then 1,2-diaminopropane with mechanical stirring. The mixture became an orange solution after about 10 minutes. The solution was then stirred at room temperature for 2.5 hours.

To the mixture was then added methanol (1400 mL) over 5 to 10 minutes. During addition, the solution became by weight; purity-corrected recovery was 77%) and was 98+% pure by HPLC (TFASH method). Pd content was 7 ppm.

A portion of the product (13 g) was charged to a flask and methanol (130 mL) was added while stirring under an atmosphere of nitrogen. The mixture was heated to 65° C., and mechanically stirred for 10 h. The mixture remained a suspension of solids throughout the reslurry. Note, about 5 to 10 minutes after MeOH was added, an apparent physical form change took place, resulting in a rapid change from a thin slurry to a very thick one that did not stir well at room temperature (the slurry itself was not actually thicker, but the new form solids appeared to be needle-like crystals and thus their volume expanded considerably). Stirring quickly improved on heating and the mixture remained an easily stir-able slurry both at elevated temperature and on cooling back to 25° C.

The mixture was then cooled to room temperature and stirred for 3 h. The solids were collected by filtration and were pulled dry on the filter via suction. The filter cake was not washed. The solids were dried in a vacuum oven at 65° C. for 18 h. The resulting white solid weighed 12.2 g (94% recovery by weight; purity-corrected recovery was 95%) and was 99+% pure by HPLC (TFASH method). Pd content was 7 ppm.

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

What is claimed is:

1. A method of preparing a compound of formula 1-a,

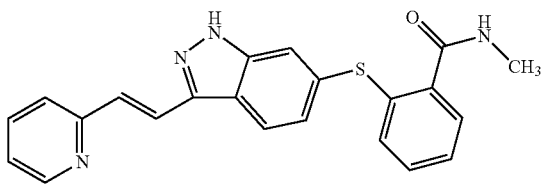

or a pharmaceutically acceptable salt thereof, the method comprising reacting a compound of formula 2-a with a compound of formula 6

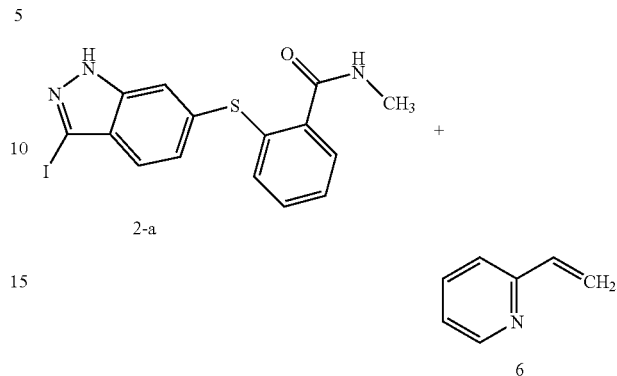

to form the compound of formula 1-a.

2. The method of claim 1, wherein the reaction is carried out under conditions comprising Pd or Cu as a catalyst.

3. The method of claim 2, wherein the catalyst is Pd(OAc)$_2$, and wherein the reaction conditions further comprise P(o-Tol)$_3$ as a ligand that complexes with the Pd catalyst.

4. The method of claim 3, wherein the reaction conditions further comprise Proton Sponge as a base, LiBr as an additive, and dimethylacetamide or N-methyl-2-pyrrolidone as a solvent, and wherein the reaction is carried out at a temperature of 100 to 120° C.

* * * * *